(12) United States Patent
Browning

(10) Patent No.: US 9,060,838 B2
(45) Date of Patent: *Jun. 23, 2015

(54) TISSUE SUPPORTED IMPLANTABLE DEVICE

(75) Inventor: James Browning, Glasgow (GB)

(73) Assignee: Coloplast A/S, Humlebaek (DK)

( * ) Notice: Subject to any disclaimer, the term of this patent is extended or adjusted under 35 U.S.C. 154(b) by 188 days.

This patent is subject to a terminal disclaimer.

(21) Appl. No.: 13/451,590

(22) Filed: Apr. 20, 2012

(65) Prior Publication Data

US 2012/0199133 A1  Aug. 9, 2012

Related U.S. Application Data

(63) Continuation of application No. 13/096,582, filed on Apr. 28, 2011, now Pat. No. 8,215,310, which is a continuation of application No. 11/597,018, filed as application No. PCT/GB2005/002026 on May 23, 2005, now Pat. No. 7,975,698.

(30) Foreign Application Priority Data

May 21, 2004 (GB) .................................. 0411360.1

(51) Int. Cl.
*A61F 6/06* (2006.01)
*A61B 17/08* (2006.01)
(Continued)

(52) U.S. Cl.
CPC ............. *A61F 2/0045* (2013.01); *A61F 2/0054* (2013.01); *A61B 17/122* (2013.01); *A61F 2/3094* (2013.01); *A61F 6/225* (2013.01)

(58) Field of Classification Search
CPC ...................................... A61F 2/0054
USPC ............... 128/830, 834, 885; 600/29, 30; 606/151, 157, 185; 623/23.72, 23.57
See application file for complete search history.

(56) References Cited

U.S. PATENT DOCUMENTS 2,738,790 A  3/1956 Todt, Sr. et al.
3,054,406 A  9/1962 Usher
(Continued)

FOREIGN PATENT DOCUMENTS

DE  2305815 A1  8/1974
DE  4220283 A1  12/1993
(Continued)

OTHER PUBLICATIONS

Abdel-fattah, Mohamed et al. Evaluation of transobturator tapes (E-TOT) study: randomised prospective single-blinded study comparing inside-out vs. outside-in transobturator tapes in management of urodynamic stress incontinence: Short term outcomes, European Journal of Obstetrics & Gynecology and Reproductive Biology (2009).

(Continued)

*Primary Examiner* — Alireza Nia
*Assistant Examiner* — Tarla Patel
(74) *Attorney, Agent, or Firm* — Coloplast Corp., Coloplast A/S; Nick Baumann

(57) ABSTRACT

An implant configured to treat prolapse of a pelvic organ includes a support member and an extension portion projecting from the support member. The extension portion has a barbed fixation means provided thereon for anchoring the extension portion into pelvic paravaginal tissue. The barbed fixation means allow bi-directional adjustment of the barbed fixation means relative to the tissue, and when suitably located, the barbed fixation means engage the tissue. The support member comprises a mesh material having a mass density of less than 50 g/m$^2$.

15 Claims, 4 Drawing Sheets

(51) Int. Cl.
*A61F 2/28* (2006.01)
*A61F 2/00* (2006.01)
A61B 17/122 (2006.01)
A61F 2/30 (2006.01)
A61F 6/22 (2006.01)

(56) References Cited

U.S. PATENT DOCUMENTS

| | | |
|---|---|---|
| 3,124,136 A | 3/1964 | Usher |
| 3,182,662 A | 5/1965 | Shirodkar |
| 3,311,110 A | 3/1967 | Singerman et al. |
| 3,384,073 A | 5/1968 | Winkle, Jr. |
| 3,472,232 A | 10/1969 | Pendleton |
| 3,580,313 A | 5/1971 | McKnight |
| 3,763,860 A | 10/1973 | Clarke |
| 3,789,828 A | 2/1974 | Schulte |
| 3,858,783 A | 1/1975 | Kapitanov et al. |
| 3,888,975 A | 6/1975 | Ramwell |
| 3,911,911 A | 10/1975 | Scommegna |
| 3,913,573 A | 10/1975 | Gutnick |
| 3,916,899 A | 11/1975 | Theeuwes et al. |
| 3,924,633 A | 12/1975 | Cook et al. |
| 3,993,058 A | 11/1976 | Hoff |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,233,968 A | 11/1980 | Shaw, Jr. |
| 4,235,238 A | 11/1980 | Ogiu et al. |
| 4,246,660 A | 1/1981 | Wevers |
| 4,441,497 A | 4/1984 | Paudler |
| 4,444,933 A | 4/1984 | Columbus et al. |
| 4,509,516 A | 4/1985 | Richmond |
| 4,632,100 A | 12/1986 | Somers et al. |
| 4,633,873 A | 1/1987 | Dumican et al. |
| 4,646,731 A | 3/1987 | Brower |
| 4,655,221 A | 4/1987 | Devereux |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |
| 4,920,986 A | 5/1990 | Biswas |
| 4,938,760 A | 7/1990 | Burton et al. |
| 5,013,292 A | 5/1991 | Lemay |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,149,329 A | 9/1992 | Richardson |
| 5,188,636 A | 2/1993 | Fedotov |
| 5,207,694 A | 5/1993 | Broome |
| 5,209,756 A | 5/1993 | Seedhom et al. |
| 5,250,033 A | 10/1993 | Evans et al. |
| 5,256,133 A | 10/1993 | Spitz |
| 5,259,835 A | 11/1993 | Clark et al. |
| 5,281,237 A | 1/1994 | Gimpelson |
| 5,328,077 A | 7/1994 | Lou |
| 5,336,239 A | 8/1994 | Gimpelson |
| 5,337,736 A | 8/1994 | Reddy |
| 5,342,376 A | 8/1994 | Ruff |
| 5,362,294 A | 11/1994 | Seitzinger |
| 5,368,595 A | 11/1994 | Lewis |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,434,146 A | 7/1995 | Labrie et al. |
| 5,439,467 A | 8/1995 | Benderev et al. |
| 5,456,711 A | 10/1995 | Hudson |
| 5,486,197 A | 1/1996 | Le et al. |
| 5,507,754 A | 4/1996 | Green et al. |
| 5,507,796 A | 4/1996 | Hasson |
| 5,520,700 A | 5/1996 | Beyar et al. |
| 5,522,896 A | 6/1996 | Prescott |
| 5,544,664 A | 8/1996 | Benderev et al. |
| 5,549,619 A | 8/1996 | Peters et al. |
| 5,562,685 A | 10/1996 | Mollenauer et al. |
| 5,562,689 A | 10/1996 | Green et al. |
| 5,569,273 A | 10/1996 | Titone et al. |
| 5,571,139 A | 11/1996 | Jenkins, Jr. |
| 5,591,163 A | 1/1997 | Thompson |
| 5,611,515 A | 3/1997 | Benderev et al. |
| 5,628,756 A | 5/1997 | Barker, Jr. et al. |
| 5,645,568 A | 7/1997 | Chervitz et al. |
| 5,647,836 A | 7/1997 | Blake, III et al. |
| 5,669,935 A | 9/1997 | Rosenman et al. |
| 5,683,349 A | 11/1997 | Makower et al. |
| 5,695,525 A | 12/1997 | Mulhauser et al. |
| 5,697,931 A | 12/1997 | Thompson |
| 5,697,978 A | 12/1997 | Sgro |
| 5,720,766 A | 2/1998 | Zang et al. |
| 5,749,884 A | 5/1998 | Benderev et al. |
| 5,766,221 A | 6/1998 | Benderev et al. |
| 5,807,403 A | 9/1998 | Beyar et al. |
| 5,816,258 A | 10/1998 | Jervis |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,851,229 A | 12/1998 | Lentz et al. |
| 5,860,425 A | 1/1999 | Benderev et al. |
| 5,899,909 A | 5/1999 | Claren et al. |
| 5,904,692 A | 5/1999 | Steckel et al. |
| 5,919,232 A | 7/1999 | Chaffringeon et al. |
| 5,922,026 A | 7/1999 | Chin |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,988,171 A | 11/1999 | Sohn et al. |
| 5,997,554 A | 12/1999 | Thompson |
| 6,010,447 A | 1/2000 | Kardjian |
| 6,030,393 A | 2/2000 | Corlew |
| 6,031,148 A | 2/2000 | Hayes et al. |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,306 A | 4/2000 | Spielberg |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,090,116 A | 7/2000 | D'Aversa et al. |
| 6,106,545 A | 8/2000 | Egan |
| 6,110,101 A | 8/2000 | Tihon et al. |
| 6,117,067 A | 9/2000 | Gil-Vernet |
| 5,633,286 A | 10/2000 | Chen |
| 6,159,207 A | 12/2000 | Yoon |
| 6,162,962 A | 12/2000 | Hinsch et al. |
| 6,168,611 B1 | 1/2001 | Rizvi |
| 6,190,401 B1 | 2/2001 | Green et al. |
| 6,197,036 B1 | 3/2001 | Tripp et al. |
| 6,200,330 B1 | 3/2001 | Benderev et al. |
| 6,221,005 B1 | 4/2001 | Bruckner et al. |
| 6,231,496 B1 | 5/2001 | Wilk et al. |
| 6,245,082 B1 | 6/2001 | Gellman et al. |
| 6,264,676 B1 | 7/2001 | Gellman et al. |
| 6,267,772 B1 | 7/2001 | Mulhauser et al. |
| 6,273,852 B1 | 8/2001 | Lehe et al. |
| 6,287,316 B1 | 9/2001 | Agarwal et al. |
| 6,292,700 B1 | 9/2001 | Morrison et al. |
| 6,302,840 B1 | 10/2001 | Benderev |
| 6,306,079 B1 | 10/2001 | Trabucco |
| 6,319,264 B1 | 11/2001 | Tormala et al. |
| 6,328,686 B1 | 12/2001 | Kovac |
| 6,328,744 B1 | 12/2001 | Harari et al. |
| 6,334,446 B1 | 1/2002 | Beyar |

(56) References Cited

U.S. PATENT DOCUMENTS

| | | |
|---|---|---|
| 6,352,553 B1 | 3/2002 | van der Burg et al. |
| 6,355,065 B1 | 3/2002 | Gabbay |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,408,656 B1 | 6/2002 | Ory et al. |
| 6,418,930 B1 | 7/2002 | Fowler |
| 6,443,964 B1 | 9/2002 | Ory et al. |
| 6,461,332 B1 | 10/2002 | Mosel et al. |
| 6,475,139 B1 | 11/2002 | Miller |
| 6,478,727 B2 | 11/2002 | Scetbon |
| 6,478,791 B1 | 11/2002 | Carter et al. |
| 6,482,214 B1 | 11/2002 | Sidor, Jr. et al. |
| 6,491,703 B1 | 12/2002 | Ulmsten |
| 6,494,887 B1 | 12/2002 | Kaladelfos |
| 6,494,906 B1 | 12/2002 | Owens |
| 6,502,578 B2 | 1/2003 | Raz et al. |
| 6,506,190 B1 | 1/2003 | Walshe |
| 6,527,802 B1 | 3/2003 | Mayer |
| 6,530,943 B1 | 3/2003 | Hoepffner et al. |
| 6,544,273 B1 | 4/2003 | Harari et al. |
| 6,575,897 B1 | 6/2003 | Ory et al. |
| 6,575,998 B2 | 6/2003 | Beyar |
| 6,582,443 B2 | 6/2003 | Cabak et al. |
| 6,592,515 B2 | 7/2003 | Thierfelder et al. |
| 6,596,001 B2 | 7/2003 | Stormby et al. |
| 6,599,235 B2 | 7/2003 | Kovac |
| 6,599,318 B1 | 7/2003 | Gabbay |
| 6,599,323 B2 | 7/2003 | Melican et al. |
| 6,612,977 B2 | 9/2003 | Staskin et al. |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,652,450 B2 | 11/2003 | Neisz et al. |
| 6,652,595 B1 | 11/2003 | Nicolo |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,679,896 B2 | 1/2004 | Gellman et al. |
| 6,689,047 B2 | 2/2004 | Gellman |
| 6,691,711 B2 | 2/2004 | Raz et al. |
| 6,695,855 B1 | 2/2004 | Gaston |
| 6,702,827 B1 | 3/2004 | Lund et al. |
| 6,737,371 B1 | 5/2004 | Planck et al. |
| 6,755,781 B2 | 6/2004 | Gellman |
| 6,786,861 B1 | 9/2004 | Pretorius |
| 6,830,052 B2 | 12/2004 | Carter et al. |
| 6,884,212 B2 | 4/2005 | Thierfelder et al. |
| 6,911,003 B2 | 6/2005 | Anderson et al. |
| 6,932,759 B2 | 8/2005 | Kammerer et al. |
| 6,936,052 B2 | 8/2005 | Gellman et al. |
| 6,960,160 B2 | 11/2005 | Browning |
| 7,025,063 B2 | 4/2006 | Snitkin et al. |
| 7,070,556 B2 | 7/2006 | Anderson et al. |
| 7,070,558 B2 | 7/2006 | Gellman et al. |
| 7,094,199 B2 | 8/2006 | Petros et al. |
| 7,112,171 B2 | 9/2006 | Rocheleau et al. |
| 7,112,210 B2 | 9/2006 | Ulmsten et al. |
| 7,140,956 B1 | 11/2006 | Korovin et al. |
| 7,156,858 B2 | 1/2007 | Schuldt Hempe et al. |
| 7,204,802 B2 | 4/2007 | De Leval |
| 7,229,404 B2 | 6/2007 | Bouffier |
| 7,288,063 B2 | 10/2007 | Petros et al. |
| 7,290,410 B2 | 11/2007 | Meneghin et al. |
| 7,297,102 B2 | 11/2007 | Smith et al. |
| 7,326,213 B2 | 2/2008 | Benderev et al. |
| 7,347,812 B2 | 3/2008 | Mellier |
| 7,387,634 B2 | 6/2008 | Benderev |
| 7,395,822 B1 | 7/2008 | Burton et al. |
| 7,410,460 B2 | 8/2008 | Benderev |
| 7,500,945 B2 | 3/2009 | Cox et al. |
| 7,517,313 B2 | 4/2009 | Thierfelder et al. |
| 7,527,633 B2 | 5/2009 | Rioux |
| 7,559,885 B2 | 7/2009 | Merade et al. |
| 7,594,921 B2 | 9/2009 | Browning |
| 7,601,118 B2 | 10/2009 | Smith et al. |
| 7,611,454 B2 | 11/2009 | De Leval |
| 7,614,258 B2 | 11/2009 | Cherok et al. |
| 7,621,864 B2 | 11/2009 | Suslian et al. |
| 7,628,156 B2 | 12/2009 | Astani et al. |
| 7,673,631 B2 | 3/2010 | Astani et al. |
| 7,686,760 B2 | 3/2010 | Anderson et al. |
| 7,691,050 B2 | 4/2010 | Gellman et al. |
| 7,713,188 B2 | 5/2010 | Bouffier |
| 7,722,528 B2 | 5/2010 | Arnal et al. |
| 7,740,576 B2 | 6/2010 | Hodroff et al. |
| 7,766,926 B2 | 8/2010 | Bosley, Jr. et al. |
| 7,789,821 B2 | 9/2010 | Browning |
| 7,794,385 B2 | 9/2010 | Rosenblatt |
| 7,815,662 B2 | 10/2010 | Spivey et al. |
| 7,927,342 B2 | 4/2011 | Rioux |
| 7,975,698 B2 * | 7/2011 | Browning ................ 128/834 |
| 7,981,022 B2 | 7/2011 | Gellman et al. |
| 8,007,430 B2 | 8/2011 | Browning |
| 8,016,741 B2 | 9/2011 | Weiser et al. |
| 8,016,743 B2 | 9/2011 | Maroto |
| 8,047,983 B2 | 11/2011 | Browning |
| 8,092,366 B2 | 1/2012 | Evans |
| 8,118,727 B2 | 2/2012 | Browning |
| 8,118,728 B2 | 2/2012 | Browning |
| 8,123,673 B2 | 2/2012 | Browning |
| 8,128,554 B2 | 3/2012 | Browning |
| 8,162,818 B2 | 4/2012 | Browning |
| 8,167,785 B2 | 5/2012 | Browning |
| 8,182,412 B2 | 5/2012 | Browning |
| 8,182,413 B2 | 5/2012 | Browning |
| 8,215,310 B2 * | 7/2012 | Browning ................ 128/834 |
| 8,273,011 B2 | 9/2012 | Browning |
| 8,449,450 B2 | 5/2013 | Browning |
| 8,454,492 B2 | 6/2013 | Browning |
| 8,469,877 B2 | 6/2013 | Browning |
| 8,512,223 B2 | 8/2013 | Browning |
| 8,574,148 B2 | 11/2013 | Browning et al. |
| 8,668,635 B2 | 3/2014 | Browning |
| 2001/0000533 A1 | 4/2001 | Kovac |
| 2001/0018549 A1 | 8/2001 | Scetbon |
| 2001/0039423 A1 | 11/2001 | Skiba et al. |
| 2001/0049467 A1 | 12/2001 | Lehe et al. |
| 2001/0049538 A1 | 12/2001 | Trabucco |
| 2001/0051815 A1 | 12/2001 | Esplin |
| 2001/0053916 A1 | 12/2001 | Rioux |
| 2002/0005204 A1 | 1/2002 | Benderev et al. |
| 2002/0007222 A1 | 1/2002 | Desai |
| 2002/0022841 A1 | 2/2002 | Kovac |
| 2002/0028980 A1 | 3/2002 | Thierfelder et al. |
| 2002/0042658 A1 | 4/2002 | Tyagi |
| 2002/0049503 A1 | 4/2002 | Milbocker |
| 2002/0052612 A1 | 5/2002 | Schmitt et al. |
| 2002/0052654 A1 | 5/2002 | Darois et al. |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0078964 A1 | 6/2002 | Kovac et al. |
| 2002/0082619 A1 | 6/2002 | Cabak et al. |
| 2002/0083949 A1 | 7/2002 | James |
| 2002/0091298 A1 | 7/2002 | Landgrebe |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0099260 A1 | 7/2002 | Suslian et al. |
| 2002/0103542 A1 | 8/2002 | Bilbo |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0119177 A1 | 8/2002 | Bowman et al. |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |

(56) References Cited

U.S. PATENT DOCUMENTS

| | | |
|---|---|---|
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz et al. |
| 2002/0183588 A1 | 12/2002 | Fierro |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz et al. |
| 2003/0023137 A1 | 1/2003 | Gellman |
| 2003/0023138 A1 | 1/2003 | Luscombe |
| 2003/0036676 A1 | 2/2003 | Scetbon |
| 2003/0050530 A1 | 3/2003 | Neisz et al. |
| 2003/0065246 A1 | 4/2003 | Inman et al. |
| 2003/0065402 A1 | 4/2003 | Anderson et al. |
| 2003/0069469 A1 | 4/2003 | Li |
| 2003/0078468 A1 | 4/2003 | Skiba et al. |
| 2003/0100954 A1 | 5/2003 | Schuldt Hempe et al. |
| 2003/0130670 A1 | 7/2003 | Anderson et al. |
| 2003/0149440 A1 | 8/2003 | Kammerer et al. |
| 2003/0171644 A1 | 9/2003 | Anderson et al. |
| 2003/0176875 A1 | 9/2003 | Anderson et al. |
| 2003/0191360 A1 | 10/2003 | Browning |
| 2003/0199732 A1 | 10/2003 | Suslian et al. |
| 2003/0212305 A1 | 11/2003 | Anderson et al. |
| 2003/0220538 A1 | 11/2003 | Jacquetin |
| 2004/0029478 A1 | 2/2004 | Planck et al. |
| 2004/0034373 A1 | 2/2004 | Schuldt-Hempe et al. |
| 2004/0039453 A1 | 2/2004 | Anderson et al. |
| 2004/0059356 A1 | 3/2004 | Gingras |
| 2004/0097974 A1 | 5/2004 | De Leval |
| 2004/0106847 A1 | 6/2004 | Benderev |
| 2004/0144395 A1 | 7/2004 | Evans et al. |
| 2004/0172048 A1* | 9/2004 | Browning ............ 606/151 |
| 2004/0231678 A1 | 11/2004 | Fierro |
| 2004/0243166 A1 | 12/2004 | Odermatt et al. |
| 2004/0249240 A1 | 12/2004 | Goldmann et al. |
| 2004/0249373 A1 | 12/2004 | Gronemeyer et al. |
| 2004/0249397 A1 | 12/2004 | Delorme et al. |
| 2004/0249473 A1 | 12/2004 | Delorme et al. |
| 2005/0000524 A1 | 1/2005 | Cancel et al. |
| 2005/0004576 A1 | 1/2005 | Benderev |
| 2005/0080317 A1 | 4/2005 | Merade |
| 2005/0107805 A1 | 5/2005 | Bouffier et al. |
| 2005/0240076 A1 | 10/2005 | Neisz et al. |
| 2005/0277806 A1 | 12/2005 | Cristalli |
| 2005/0278037 A1 | 12/2005 | Delorme et al. |
| 2005/0283040 A1 | 12/2005 | Greenhalgh |
| 2006/0025649 A1 | 2/2006 | Smith et al. |
| 2006/0025783 A1 | 2/2006 | Smith et al. |
| 2006/0041185 A1 | 2/2006 | Browning |
| 2006/0058578 A1 | 3/2006 | Browning |
| 2006/0089524 A1 | 4/2006 | Chu |
| 2006/0089525 A1 | 4/2006 | Mamo et al. |
| 2006/0130848 A1 | 6/2006 | Carey |
| 2006/0205995 A1 | 9/2006 | Browning |
| 2006/0264698 A1 | 11/2006 | Kondonis et al. |
| 2007/0015953 A1 | 1/2007 | MacLean |
| 2007/0020311 A1 | 1/2007 | Browning |
| 2007/0032695 A1 | 2/2007 | Weiser |
| 2007/0032881 A1 | 2/2007 | Browning |
| 2007/0059199 A1 | 3/2007 | Labuschagne |
| 2007/0149555 A1 | 6/2007 | Kase et al. |
| 2007/0219606 A1 | 9/2007 | Moreci et al. |
| 2008/0021263 A1 | 1/2008 | Escude et al. |
| 2008/0161837 A1 | 7/2008 | Toso et al. |
| 2008/0167518 A1 | 7/2008 | Burton et al. |
| 2008/0196729 A1 | 8/2008 | Browning |
| 2008/0200751 A1 | 8/2008 | Browning |
| 2009/0123522 A1 | 5/2009 | Browning |
| 2009/0137862 A1 | 5/2009 | Evans et al. |
| 2009/0171377 A1 | 7/2009 | Intoccia et al. |
| 2009/0221868 A1 | 9/2009 | Evans |
| 2009/0287229 A1 | 11/2009 | Ogdahl |
| 2010/0022822 A1 | 1/2010 | Walshe |
| 2010/0056856 A1 | 3/2010 | Suslian et al. |
| 2010/0113869 A1 | 5/2010 | Goldman |
| 2010/0130814 A1 | 5/2010 | Dubernard |
| 2010/0198002 A1 | 8/2010 | O'Donnell |
| 2010/0222794 A1 | 9/2010 | Browning |
| 2010/0256442 A1 | 10/2010 | Ogdahl et al. |
| 2010/0274074 A1 | 10/2010 | Khamis et al. |
| 2010/0280308 A1 | 11/2010 | Browning |
| 2010/0298630 A1 | 11/2010 | Wignall |
| 2011/0021868 A1 | 1/2011 | Browning |
| 2011/0034759 A1 | 2/2011 | Ogdahl et al. |
| 2011/0105833 A1 | 5/2011 | Gozzi et al. |
| 2011/0124954 A1 | 5/2011 | Ogdahl et al. |
| 2011/0124956 A1 | 5/2011 | Mujwid et al. |
| 2011/0201872 A1 | 8/2011 | Browning |
| 2011/0230705 A1 | 9/2011 | Browning |
| 2011/0230708 A1 | 9/2011 | Browning |
| 2011/0230709 A1 | 9/2011 | Browning |
| 2011/0237865 A1 | 9/2011 | Browning |
| 2011/0237866 A1 | 9/2011 | Browning |
| 2011/0237867 A1 | 9/2011 | Browning |
| 2011/0237868 A1 | 9/2011 | Browning |
| 2011/0237869 A1 | 9/2011 | Browning |
| 2011/0237870 A1 | 9/2011 | Browning |
| 2011/0237873 A1 | 9/2011 | Browning |
| 2011/0237874 A1 | 9/2011 | Browning |
| 2011/0237875 A1 | 9/2011 | Browning |
| 2011/0237876 A1 | 9/2011 | Browning |
| 2011/0237877 A1 | 9/2011 | Browning |
| 2011/0237878 A1 | 9/2011 | Browning |
| 2011/0237879 A1 | 9/2011 | Browning |
| 2011/0238095 A1 | 9/2011 | Browning |
| 2011/0245594 A1 | 10/2011 | Browning |
| 2011/0282136 A1 | 11/2011 | Browning |
| 2012/0143000 A1 | 6/2012 | Browning |
| 2012/0149977 A1 | 6/2012 | Browning |
| 2014/0039244 A1 | 2/2014 | Browning |
| 2014/0039247 A1 | 2/2014 | Browning |
| 2014/0039248 A1 | 2/2014 | Browning |
| 2014/0051917 A1 | 2/2014 | Browning |

FOREIGN PATENT DOCUMENTS

| | | |
|---|---|---|
| DE | 4304353 A1 | 4/1994 |
| DE | 10019604 C2 | 6/2002 |
| EP | 0009072 A1 | 4/1980 |
| EP | 0024781 B1 | 8/1984 |
| EP | 0024780 B1 | 10/1984 |
| EP | 0248544 B1 | 4/1991 |
| EP | 0139286 B1 | 8/1991 |
| EP | 0470308 A1 | 2/1992 |
| EP | 0557964 A1 | 9/1993 |
| EP | 0632999 A1 | 1/1995 |
| EP | 0650703 A1 | 5/1995 |
| EP | 0706778 A1 | 4/1996 |
| EP | 1093758 A1 | 4/2001 |
| EP | 0719527 B1 | 8/2001 |
| EP | 0643945 B1 | 3/2002 |
| EP | 1060714 B1 | 8/2006 |
| EP | 1274370 B1 | 9/2006 |
| EP | 1296614 B1 | 9/2006 |
| EP | 0797962 B2 | 9/2009 |
| FR | 1274370 A | 10/1961 |
| FR | 2712177 A1 | 5/1995 |
| FR | 2732582 A1 | 10/1997 |
| FR | 2735015 A1 | 2/1998 |
| FR | 2811218 E | 11/2000 |
| FR | 2787990 A1 | 4/2001 |
| GB | 0378288 A | 8/1932 |
| GB | 2353220 A | 2/2001 |
| RU | 2187251 C1 | 8/2002 |
| RU | 2196518 C2 | 1/2003 |
| SU | 1225547 A | 4/1986 |
| SU | 1342486 A1 | 10/1987 |
| SU | 1475607 A1 | 4/1989 |
| WO | WO9100714 A1 | 1/1991 |
| WO | WO9317635 A1 | 9/1993 |
| WO | WO9319678 A2 | 10/1993 |

(56) References Cited

FOREIGN PATENT DOCUMENTS

| | | |
|---|---|---|
| WO | WO9533454 A1 | 12/1995 |
| WO | WO9603091 A1 | 2/1996 |
| WO | WO9606567 A1 | 3/1996 |
| WO | WO9713465 A1 | 4/1997 |
| WO | WO9722310 A2 | 6/1997 |
| WO | WO9743982 A1 | 11/1997 |
| WO | WO9819606 A1 | 5/1998 |
| WO | WO9835606 A2 | 8/1998 |
| WO | WO9835616 A1 | 8/1998 |
| WO | WO9835632 A1 | 8/1998 |
| WO | WO9857590 A1 | 12/1998 |
| WO | WO9916381 A1 | 4/1999 |
| WO | WO9952450 A1 | 10/1999 |
| WO | WO9959477 A1 | 11/1999 |
| WO | WO0007520 A1 | 2/2000 |
| WO | WO0013601 A1 | 3/2000 |
| WO | WO0015141 A1 | 3/2000 |
| WO | WO0018319 A1 | 4/2000 |
| WO | WO0038784 A1 | 7/2000 |
| WO | WO0057812 A1 | 10/2000 |
| WO | WO0064370 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |
| WO | WO0139670 A1 | 6/2001 |
| WO | WO0145589 A1 | 6/2001 |
| WO | WO0152729 A2 | 7/2001 |
| WO | WO0156499 A1 | 8/2001 |
| WO | WO0180773 A1 | 11/2001 |
| WO | WO0202031 A1 | 1/2002 |
| WO | WO0226108 A2 | 4/2002 |
| WO | WO0228312 A1 | 4/2002 |
| WO | WO0230293 A1 | 4/2002 |
| WO | WO0232284 A2 | 4/2002 |
| WO | WO0232346 A1 | 4/2002 |
| WO | WO0234124 A2 | 5/2002 |
| WO | WO0239890 A2 | 5/2002 |
| WO | WO02060371 A1 | 8/2002 |
| WO | WO02065921 A1 | 8/2002 |
| WO | WO02065944 A1 | 8/2002 |
| WO | WO02069781 A2 | 9/2002 |
| WO | WO02071953 A2 | 9/2002 |
| WO | WO02078548 A1 | 10/2002 |
| WO | WO02078552 A1 | 10/2002 |
| WO | WO02078568 A1 | 10/2002 |
| WO | WO02078571 A2 | 10/2002 |
| WO | WO02098340 A1 | 12/2002 |
| WO | WO03002027 A1 | 1/2003 |
| WO | WO03013392 A1 | 2/2003 |
| WO | WO03057074 A2 | 7/2003 |
| WO | WO03022260 B1 | 10/2003 |
| WO | WO03086205 A2 | 10/2003 |
| WO | WO03092546 A2 | 11/2003 |
| WO | WO03094781 A1 | 11/2003 |
| WO | WO2004002370 A1 | 1/2004 |
| WO | WO2004002379 A1 | 1/2004 |
| WO | WO2004004600 A1 | 1/2004 |
| WO | WO2004012626 A1 | 2/2004 |
| WO | WO2004098461 A2 | 11/2004 |
| WO | WO2005018494 A1 | 3/2005 |
| WO | WO2005112842 A1 | 12/2005 |
| WO | WO2006015031 A2 | 2/2006 |
| WO | WO2006015042 A1 | 2/2006 |
| WO | WO2006136625 A1 | 12/2006 |
| WO | WO2007059199 A2 | 5/2007 |
| WO | WO2007149555 A2 | 12/2007 |
| WO | WO2008007086 A2 | 1/2008 |
| WO | WO2008018494 A1 | 2/2008 |

OTHER PUBLICATIONS

Aldridge, "Transplantation of Fascia for Relief of Urinary Stress Incontinence," Am. J. Obstet. Gynecol., 1942, 44:398-411.

Araki et al., "The Loop-Loosening Procedure for Urination Difficulties After Stamey Suspension of the Vesical Neck," J. Urol., 1990, 144:319-323.

Asmussen and Ulmsten, "Simultaneous Urethro-Cystometry with a New Technique," Scand. J. Urol. Nephrol., 1976, 10:7-11.

Beck and McCormick, "Treatment of Urinary Stress Incontinence with Anterior Colporrhaphy," Obstetrics and Gynecology, 1982, 59(3):271-274.

Benderev, "A Modified Percutaneous Outpatient Bladder Neck Suspension System," J. Urol., 1994, 152:2316-2320.

Benderev, "Anchor Fixation and Other Modifications of Endoscopic Bladder Neck Suspension," Urology, 1992, 40(5):409-418.

Bergman and Elia, "Three surgical procedures for genuine stress incontinence: Five-year follow-up of a prospective randomized study," Am. J. Obstet. Gynecol., 1995, 173:66-71.

Blaivas and Jacobs, "Pubovaginal Fascial Sling for the Treatment of Complicated Stress Urinary Incontinence," J. Urol., 1991, 145:1214-1218.

Blaivas and Salinas, "Type III Stress Urinary Incontinence: Importance of Proper Diagnosis and Treatment," American College of Surgeons Surgical Forum, 1984, 70.sup.th Annual Clinical Congress, San Francisco, CA, vol. XXXV, pp. 473-474.

Botros, Cystocele and Rectocele Repair: More Success With Mesh? Jun. 2006.

Bryans, "Marlex gauze hammock sling operation with Cooper's ligament attachment in the management of recurrent urinary stress incontinence," Am. J. Obstet. Gynecol., 1979, 133(3):292-294.

Burch, "Urethrovaginal fixation to Cooper's ligament for correction of stress incontinence, cystocele, and prolapse," Am. J. Obstet. Gynecol., 1961, 81(2):281-290.

Certified priority document for GB Application No. 0025068.8, filed Oct. 12, 2000, 38 pages.

Certified priority document for GB Application No. 0208359.0, filed Apr. 11, 2002, 50 pages.

Certified priority document for GB Application No. 0411360.1, filed May 21, 2004, 31 pages.

Chen, Biologic Grafts and Synthetic Meshes in Pelvic Reconstructive Surgery, Jun. 2007.

Choe and Staskin, "Gore-Tex Patch Sling: 7 Years Later," Urology, 1999, 54:641-646.

Chopra et al., "Technique of Rectangular Fascial Sling," Female Urology, 1996, Raz (ed.), W.B. Saunders Company, Chapter 34, pp. 392-394.

Dargent, D. et al., Pose d'un ruban sous uretral oblique par voie obturatrice dans le traitement de L'incontinence urinary feminine [English "Insertion of a transobturator oblique suburethral sling in the treatment of female urinary incontinence"], Gynecol. Obstet. Ferril. 14, pp. 576-582 (2002) [including English translation at the beginning of document].

Das and Palmer, "Laparoscopic Colpo-Suspension," J. Urol., 1995, 154:1119-1121.

de Leval, J., "Novel Surgical Technique for the Treatment of Female Stress Urinary Continence: Transobturator Vaginal Tape Inside-Out," European Urology, 2003, 44:724-730.

DeBord, James R., (1998), "The Historical Development of Prosthetics in Hernia Surgery," Surgical Clinics of North America, 78(6): 973-1006.

Decter, "Use of the Fascial Sling for Neurogenic Incontinence: Lessons Learned," J. Urol., 1993, 150:683-686.

Delmore, E. et al., La bandelette trans-obturatrice: Un procede mini-invasif pour traiter l'incontinence urinaire d'effort de la femme, Progres en Urologie, vol. 11, pp. 1306-1313 (2001) [including English translation at the beginning of document].

deTayrac, et al. Prolapse repair by vaginal route using . . . Int. Urogynecol. J. (published online May 13, 2006).

Dwyer, Transvaginal repair of anterior and posterior compartment prolapse with Atrium polypropylene mesh, BJOG: An International Journal of Obstetrics & Gynaecology, Aug. 2004.

Enzelsberger et al., "Urodynamic and Radiologic Parameters Before and After Loop Surgery for Recurrent Urinary Stress Incontinence," Acta Obstet. Gynecol. Scand., 1990, 69:51-54.

(56) References Cited

OTHER PUBLICATIONS

Eriksen et al., "Long-Term Effectiveness of the Burch Colposuspension in Female Urinary Stress Incontinence," Acta Obstet. Gynecol. Scand., 1990, 69:45-50.
Falconer et al., "Clinical Outcome and Changes in Connective Tissue Metabolism After Intravaginal Slingplasty in Stress Incontinent Women," Int. Urogynecol. J., 1996, 7:133-137.
Falconer et al., "Influence of Different Sling Materials on Connective Tissue Metabolism in Stress Urinary Incontinent Women," Int. Urogynecol. J., 2001, (Suppl. 2):S19-S23.
Gilja et al., "A Modified Raz Bladder Neck Suspension Operation (Transvaginal Burch)," J. Urol., 1995, 153:1455-1457.
Gittes and Loughlin, "No-Incision Pubovaginal Suspension for Stress Incontinence," J. Urol., 1987, 138:568-570.
Gruss, "The Obturator Bypass. Indications. Techniques. Outcomes," Chirurgie, 1971, 97:220-226.
Guida and Moore, "The Surgeon At Work. Obturator Bypass Technique," Surgery, Gynecology & Obstetrics, 1969, pp. 1307-1315.
Handa et al., "Banked Human Fascia Lata for the Suburethral Sling Procedure: A Preliminary Report," Obstet. Gynecol., 1996, 88:1045-1049.
Hardiman, et al. Cystocele repair using polypropylene mesh. Br. J. Obstet. Gynaecol. 107: 825-26 (2000).
Henriksson and Ulmsten, "A urodynamic evaluation of the effects of abdominal urethrocystopexy and vaginal sling urethroplasty in women with stress incontinence," Am. J. Obstet. Gynecol., 1978, 131:77-82.
Hodgkinson and Kelly, "Urinary Stress Incontinence in the Female. III. Round-ligament technique for retropubic suspension of the urethra," Obstet. Gynecol., 1957, 10:493-499.
Hohenfellner and Petri, "Sling Procedures," Surgery of Female Incontinence, 2nd edition, SpringerVeriag, pp. 105-113, 1986.
Holschneider et al., "The Modified Pereyra Procedure in Recurrent Stress Urinary Incontinence: A 15-Year Review," Obstet. Gynecol., 1994, 83:573-578.
Horbach et al., "A Suburethral Sling Procedure with Polytetrafluoroethylene for the Treatment of Genuine Stress Incontinence in Patients with Low Urethral Closure Pressure," Obstet. Gynecol., 1988, 71:648-652.
Horbach, "Suburethral Sling Procedures," Urogynecology and Urodynamics-Theory and Practice, 1996, Williams & Wilkins, pp. 569-579.
Ingelman-Sundberg and Ulmsten, "Surgical Treatment of Female Urinary Stress Incontinence," Contr. Gynec. Obstet., 1983, 10:51-69.
International Preliminary Examination Report issued in PCT/GB01/04554, completed Nov. 22, 2002, 6 pages.
International Search Report for PCT/GB2009/050174, mailed Jun. 24, 2009.
International Search Report issued in PCT/GB01/04554, mailed Jan. 29, 2002, 3 pages.
International Search Report issued in PCT/GB2007/002589, mailed Jan. 22, 2008, 5 pages.
Jacquetin, Bernard, "2. Utilisation du "TVT" dans la chirurgie de l'incontinence urinaire feminine", J. Gynecol. Obstet. Biol. Reprod. 29: 242-47 (2000).
Jeffcoate, "The Results of the Aldridge Sling Operation for Stress Incontinence," The Journal of Obstetrics and Gynaecology of the British Empire, 1956, 63:36-39.
Ulmsten et al., "An Ambulatory Surgical Procedure Under Local Anesthesia for Treatment of Female Urinary Incontinence," Int. Urogynecol. J., 1996, 7:81-86.
Ulmsten et al., "Different Biochemical Composition of Connective Tissue in Continent and Stress Incontinent Women," Acta Obstet. Gynecol. Scand., 1987, 66:455-457.
Ulmsten et al., "The unstable female urethra," Am. J. Obstet. Gynecol., 1982, 144:93-97.
Ulmsten, "Female Urinary Incontinence—A Symptom, Not a Urodynamic Disease. Some Theoretical and Practical Aspects on the Diagnosis and Treatment of Female Urinary Incontinence," Int. Urogynecol. J., 1995, 6:2-3.
Ulstem et al., "A Multicenter Study of Tension-Free Vaginal Tape (TVT) for Surgical Treatment of Stress Urinary Incontinence," Int. Urogynecol. J., 1998, 9:210-213.
U.S. Appl. No. 13/149,994, filed Jun. 1, 2011.
U.S. Appl. No. 10/106,086, filed Mar. 25, 2002.
U.S. Appl. No. 11/199,061, filed Aug. 8, 2005.
U.S. Appl. No. 60/279,794, filed Mar. 29, 2001.
U.S. Appl. No. 60/302,929, filed Jul. 3, 2001.
U.S. Appl. No. 60/307,836, filed Jul. 25, 2001.
U.S. Appl. No. 60/322,309, filed Sep. 14, 2001.
U.S. Appl. No. 60/362,806, filed Mar. 7, 2002.
U.S. Appl. No. 60/380,797, filed May 14, 2002.
U.S. Appl. No. 60/393,969, filed Jul. 5, 2002.
U.S. Appl. No. 60/402,007, filed Aug. 8, 2002.
U.S. Appl. No. 60/414,865, filed Sep. 30, 2002.
Webster and Kreder, "Voiding Dysfunction Following Cystourethropexy: Its Evaluation and Management," J. Urol., 1990, 144:670-673.
Weidemann, Small Intestinal Submucosa for Pubourethral Sling Suspension for the Treatment of Stress Incontinence: First Histopathological Results in Humans, Jul. 2004.
Winter, "Peripubic Urethropexy for Urinary Stress Incontinence in Women," Urology, 1982, 20(4):408-411.
Woodside and Borden, "Suprapubic Endoscopic Vesical Neck Suspension for the Management of Urinary Incontinence in Myelodysplastic Girls," J. Urol., 1986, 135:97-99.
Written Opinion for PCT/GB2009/050174, mailed Jun. 24, 2009.
Written Opionion issued in PCT/GB2007/002589, mailed Jan. 22, 2008, 5 pages.
Zacharin and Hamilton, "Pulsion Enterocele: Long-Term Results of an Abdominoperineal Technique," Obstet. Gynecol., 1980, 55(2):141-148.
Zacharin, "The suspensory mechanism of the female urethra," J. Anat., 1963, 97(3):423-427.
Pereyra et al., "Pubourethral Supports in Perspective: Modified Pereyra Procedure for Urinary Incontinence," Obstet Gynecol., 1982, 59:643-648.
Petros and Konsky, "Anchoring the midurethra restores bladder-neck anatomy and continence," The Lancet, 1999, 354:997-998.
Petros and Ulmsten, "An analysis of rapid pad testing and the history for the diagnosis of stress incontinence," Acta Obstet. Gynecol. Scand., 1992, 71:529-536.
Petros and Ulmsten, "An Anatomical Basis for Success and Failure of Female Incontinence Surgery," Scand. J. Urol. Nephrol., 1993, (Suppl. 3):55-60.
Petros and Ulmsten, "An Integral Theory and Its Method for the Diagnosis and Management of Female Urinary Incontinence," 153 Scand. J. Urol. Nephrol. 1, 64 (1993).
Petros and Ulmsten, "An Integral Theory of Female Urinary Incontinence," Acta Obstet. Gynecol. Scand., 1990, 69(Suppl.153):7-31.
Petros and Ulmsten, "Bladder Instability in Women: A Premature Activation of the Micturition Reflex," Neurourology and Urodynamics, 1993, 12:235-239.
Petros and Ulmsten, "Cough Transmission Ratio: An Indicator of Suburethral Vaginal Wall Tension Rather than Urethral Closure?" Acta Obstet. Gynecol. Scand., 1990, 69(Suppl. 153):37-38.
Petros and Ulmsten, "Cure of Stress Incontinence by Repair of External Anal Sphincter," Acta. Obstet. Gynecol Scand., 1990, 69(Suppl. 153):75.
Petros and Ulmsten, "Cure of Urge Incontinence by the Combined Intravaginal Sling and Tuck Operation," Acta Obstet. Gynecol. Scand., 1990, 69(Suppl. 153)61-62.
Petros and Ulmsten, "Further Development of the Intravaginal Slingplasty Procedure—IVS III—(with midline "tuck")," Scand. J. Urol. Nephrol., 1993, Suppl. 153:69-71.
Petros and Ulmsten, "Non Stress Non Urge Female Urinary Incontinence—Diagnosis and Cure: A Preliminary Report," Acta Obstet. Gynecol. Scand., 1990, 69(Suppl. 153):69-70.
Petros and Ulmsten, "Part I: Theoretical, Morphological, Radiographical Correlations and Clinical Perspective," Scand. J. Urol. Nephrol., 1993, Suppl. 153:5-28.

(56) References Cited

OTHER PUBLICATIONS

Petros and Ulmsten, "Part II:The Biomechanics of Vaginal Tissue and supporting Ligaments with Special Relevance to the Pathogenesis of Female Urinary Incontinence," Scand. J. Urol. Nephrol., 1993, Suppl. 153:29-40.
Petros and Ulmsten, "Part III: Surgical Principles Deriving from the Theory," Scand. J. Urol. Nephrol., 1993, Suppl. 153:41-52.
Petros and Ulmsten, "Part IV: Surgical Applications of the Theory—Development of the Intravaginal Sling Plasty (IVS) Procedure," Scand. J. Urol. Nephrol., 1993, Suppl. 153:53-54.
Petros and Ulmsten, "Pinch Test for Diagnosis of Stress Urinary Incontinence," Acta Obstet. Gynecol. Scand., 1990, 69(Suppl. 153):33-35.
Petros and Ulmsten, "Pregnancy Effects on the Intravaginal Sling Operation," Acta Obstet. Gynecol. Scand., 1990, 69(Suppl.153):77-78.
Petros and Ulmsten, "The Combined Intravaginal Sling and Tuck Operation. An Ambulatory Procedure for Cure of Stress and Urge Incontinence," Acta Obstet. Gynecol. Scand., 1990, 69(Suppl. 153):53-59.
Petros and Ulmsten, "The Development of the Intravaginal Slingplasty Procedure: IVS II—(with bilateral "tucks")," Scand. J. Urol. Nephrol., 1993, Suppl. 153:61-67.
Petros and Ulmsten, "The Free Graft Procedure for Cure of the Tethered Vagina Syndrome," Scand. J. Urol. Nephrol., 1993, Suppl. 153:85-87.
Petros and Ulmsten, "The Further Development of the Intravaginal Slingplasty Procedure: IVS IV—(with "double-breasted" unattached vaginal flap repair and "free" vaginal tapes)," Scand. J. Urol. Nephrol., 1993, Suppl. 153:73-79.
Petros and Ulmsten, "The Intravaginal Slingplasty Procedure: Ivs V1—further development of the "double-breasted" vaginal flap repair—attached flap," Scand. J. Urol. Nephrol., 1993, Suppl. 153:81-84.
Petros and Ulmsten, "The Posterior Fornix Syndrome: A Multiple Symptom Complex of Pelvin Pain and Abnormal Urinary Symptoms Deriving from Laxity in the Posterior Fornix of Vagina," Scand. J. Urol. Nephrol., 1993, Suppl. 153:89-93.
Petros and Ulmsten, "The Role of a Lax Posterior Vaginal Fornix in the Causation of Stress and Urgency Symptoms: a Preliminary Report," Acta Obstet. Gynecol. Scand., 1990, 69(Suppl. 153):71-73.
Petros and Ulmsten, "The Tethered Vagina Syndrome, Post Surgical Incontinence and I-Plasty Operation for Cure," Acta Obstet. Gynecol Scand., 1990, 69(Suppl.153):63-67.
Petros and Ulmsten, "The Tuck Procedure: A Simplified Vaginal Repair for Treatment of Female Urinary Incontinence," Acta Obstet. Gynecol. Scand., 1990, 69(Suppl.153):41-42.
Petros and Ulmsten, "Urethral Pressure Increase on Effort Originates From Within the Urethra, and Continence From Musculovaginal Closure," Neurourology and Urodynamics, 1995, 14:337-350.
Petros et al., "The Autogenic Ligament Procedure: A Technique for Planned Formation of an Artificial Neo-Ligament," Acta Obstet. Gynecol. Scand., 1990, 69(Suppl. 153):43-51.
Petros, "Development of Generic Models for Ambulatory Vaginal Surgery—a Preliminary Report," Int. Urogynecol. J., 1998, 9:19-27.
Product Monograph for Aris Transobturator Tape for the Treatment of Female Stress Urinary Incontinence, 2004, 40 pages.
Rackley et al., "Tension-free Vaginal Tape and Percutaneous Vaginal Tape Sling Procedures," Techniques in Urology, 2001, 7(2):90-100.
Rackley, "Synthetic slings: Five steps for successful placement—Follow these steps to insert Transvaginal/Percutaneous slings using vaginal approach alone," Urology Times, 2000, 28:46-49.
Raz et al., "Urological Neurology and Urodynamics," J. Urol., 1992, 148:845-850.
Raz, "Modified Bladder Neck Suspension for Female Stress Incontinence," Urology, 1981, 17(1):82-85.
Richardson et al., "Delayed Reaction to the Dacron Buttress Used in Urethropexy," J. Reproductive Med., 1984, 29(9):689-692.
Ridley, "Appraisal of the Goebell-Frangenheim-Stoeckel sling procedure," Am. J. Obstet. Gynecol., 1966, 95(5):714-721.
Schumpelick, V. et at., "Minimized polypropylene mesh for preperitoneal net plasty (PNP) of incisional hernias," Chirurg 70:422-430 (1999).
Shaw, W., "An Operation for the Treatment of Stress Incontinence," Br. Med. J. 1949:1070-1073.
Sheiner et al., "An unusual complication of obturator foramen arterial bypass," J. Cardiovasc. Surg., 1969, 10(4):324-328.
Sirls and Leach, "Use of Fascia Lata for Pubovaginal Sling," Female Urology, 1996, Raz (ed.). W.B. Saunders Company, Chapter 32, pp. 376-381.
Sloan and Barwin, "Stress Incontinence of Urine: A Retrospective Study of the Complications and Late Results of Simple Suprapubic Suburethral Fascial Slings," J. Urol., 1973, 110:533-536.
Spencer et al., "A Comparison of Endoscopic Suspension of the Vesical Neck with Suprapubic Vesicourethropexy for Treatment of Stress Urinary Incontinence," J. Urol., 1987, 137:411-415.
Spinosa, JP et al., Transobturator surgery for female stress incontinence: a comparative anatomical study of outside-in vs. inside-out techniques, BJU Intl., 100(5), pp. 1097-1102 (Nov. 2007).
Stamey, "Endoscopic Suspension of the Vesical Neck for Urinary Incontinence in Females," Annals of Surgery, 1980, 192(4):465-471.
Stanton, "Suprapubic Approaches for Stress Incontinence in Women," J. Am. Geriatrics Soc., 1990, 38(3):348-351.
Staskin et al., "The Gore-tex sling procedure for female sphincteric incontinence: indications, technique, and results," World J. Urol., 1997, 15:295-299.
Stothers et al., "Anterior Vaginal Wall Sling," Female Urology, 1996, Raz (ed.), W.B. Saunders Company, Chapter 35, pp. 395-398.
Ulmsten and Petros, "Intravaginal Slingplasty (IVS): An Ambulatory Surgical Procedure for Treatment of Female Urinary Incontinence," Scand. J. Urol. Nephrol., 1995, 29:75-82.
Ulmsten et al., "A three-year follow up of tension free vaginal tape for surgical treatment of female stress urinary incontinence," Br. J. Obstet. Gynecol., 1999, 106:345-350.
International Search Report and Written Opinion issued in PCT/GB2004/001390, mailed Sep. 3, 2004, 12 pages.
BioArc(R) SP Sling Kit: 12 Step Procedure, American Medical Systems Inc. Online Brochure 2006, 2 pages.
Jeter, "The Social Impact of Urinary Incontinence," Female Urology, Raz (ed.), W. B. Saunders Company, 1996, Chapter 7, pp. 80-86.
Karram and Bhatia, "Patch Procedure: Modified Transvaginal Fascia Lata Sling for Recurrent or Severe Stress Urinary Incontinence," Obstet Gynecol., 1990, 75:461-463.
Kerdiles et al., "Bypass via the Obturator Foramen in Reconstructive Arterial Surgery of the Lower Extremities," Ann. Chir. Thorac. Cardio-Vasc., 1974, 13(4):335-341.
Kerr and Staskin, "The Use of Artificial Material for Sling Surgery in the Treatment of Female Stress Urinary Incontinence," Female Urology, 1996, Raz (ed.), W.B. Saunders Company, Chapter 33, pp. 382-391.
Kersey, "The gauze hammock sling operation in the treatment of stress incontinence," Br. J. Obstet. Gynecol., 1983, 90:945-949.
Klinge et al., "Functional and Morphological Evaluation of a Low-Weight, Monofilament Polypropylene Mesh for Hernia Repair," Journal of Biomedical Material Research, Jan. 24, 2002, pp. 129-137.
Klinge, U. et al., "Influence of polyglactin-coating on functional and morphological parameters of polypropylene-mesh modifications for abnormal wall repair," Biomaterials 20 (1999), pp. 613-623.
Klinge, U. et al., "Modified Mesh for Hernia Repair that is Adapted to the Physiology of the Abdominal Wall," Eur J Surg 164:951-960 (1998).
Klinge, U. et al., "Pathophysiology of the abdominal wall," Der Chirurg, (1996),67: 229-233.
Klosterhalfen, B, et al., "Functional and morphological evaluation of different polypropylene-mesh modifications for abdominal wall repair," Biomaterials 19:2235-2246 (1998).
Klosterhalfen, B. et al., "Morphological correlation of the functional mechanics of the abdominal wall after mesh implantation," Langenbecks Arch Chir 382:87-94 (1997).
Klutke et al., "The Anatomy of Stress Incontinence: Magnetic Resonance Imaging of the Female Bladder Neck and Urethra," J. Urol., 1990, 143:563-566.

(56) References Cited

OTHER PUBLICATIONS

Klutke et al., "Transvaginal Bladder Neck Suspension to Cooper's Ligament: A Modified Pereyra Procedure," Obstet. GynecoL, 1996, 88:294-297.
Korda et al., "Experience with Silastic Slings for Female Urinary Incontinence," Aust. Nz J. Obstet. Gynaecol., 1989, 29:150-154.
Kovac and Cruikshank, "Pubic Bone Suburethral Stabilization Sling for Recurrent Urinary Incontinence," Obstet. GynecoL, 1997, 89:624-62T.
Kovac and Cruikshank, "Pubic bone suburethral stabilization sling: a long-term cure for SUI?" Contemporary OB/GYN, 1998, 43(2):51-72.
Kovac, "Follow-up of the Pubic Bone Suburethral Stabilization Sling Operation for Recurrent Urinary Incontinence (Kovac Procedure)," J. Pelvic Surgery, 1999, 5(3):156-160.
Lazarevski, M.B., Suburethral Duplication of the Vaginal Wal—An Original Operation for Urinary Stress Incontinence in Women, 6 Int'l Urogynecol. J. 73 -79 (1995).
Leach et al., "Female Stress Urinary Incontinence Clinical Guidelines Panel Summary Report on Surgical Management of Female Stress Urinary Incontinence," J. Urol., 1997, 158:875-880.
Leach, "Bone Fixation Technique for Transvaginal Needle Suspension," Urology, 1988, 31(5):388-390.
Lichtenstein et al., "The Tension-Free Hernioplasty," Am. J. Surgery, 1989, 157:188-193.
Lipton, S. And Estrin, J., "A Biomechanical Study of the Aponeurotic Iguinal Hernia Repair," Journal of the American College of Surgeons, Jun. 1994, vol. 178, pp. 595-599.
Loughlin et al., "Review of an 8-Year Experience with Modifications of Endoscopic Suspension of the Bladder Neck for Female Stress Urinary Incontinence," J. Urol., 1990, 143:44-45.
Maher, Surgical Management of Anterior Vaginal Wall Prolapse: An Evidence Based Literature Review, 2006.
Mahoney and Whelan, "Use of Obturator Foramen in Iliofemoral Artery Grafting: Case Reports," Annals of Surgery, 1966, 163(2):215-220.
Marshall et al., "The Correction of Stress Incontinence by Simple Vesicourethral Suspension," J. Urol., 2002, 168:1326-1331.
McGuire and Gormley, "Abdominal Fascial Slings," Female Urology, 1996, Raz (ed.), W.B. Saunders Company, Chapter 31, pp. 369-375.
McGuire and Lytton, "Pubovaginal Sling Procedure for Stress Incontinence," J. Urol., 1978, 119:82-84.
McGuire et al., "Experience with Pubovaginal Slings for Urinary Incontinence at the University of Michigan," J. Urol., 1987, 138:525-526.
McGuire, "Abdominal Procedures for Stress Incontinence," Urologic Clinics of North America, 1985, 12(2):285-290.
Mclndoe et al., "The Aldridge Sling Procedure in the Treatment of Urinary Stress Incontinence," Aust. NZ J. Obstet. Gynaecol., 1987, 27:238-239.
McKiel, Jr. et al., "Marshall-Marchetti Procedure: Modification," J. Urol., 1966, 96:737-739.
Miklos, Mini Sling Incontinence Treatment—Vagina Plastic Surgery, http://www.miklosandmoore.com/mini_sling.php, Feb. 28, 2011.
MiniArc Single-Incision Sling http://www.americanmedicalsystems.com Mar. 4, 2011.
Moir, "The Gauze-Hammock Operation," the Journal of Obstetrics and Gynaecology of the British Commonwealth, 1968, 75(1):1-9.
Monseur, J., Anatomie Chirurgicale: Les Ligaments Du Perinee Feminin, Sep. 4, 2008.
Moore et al. "Single-Center Retrospective Study of the Technique, Safety, and 12 Month Efficacy or the MiniArc™ Single Incision Sling: A New Minimally Invasive Procedure for Treatment of Female SUI" [Online] 2009, 18, pp. 175-81.
Morgan et al., "The Marlex sling operation for the treatment of recurrent stress urinary incontinence: A 16-year review," Am. J. Obstet. Gynecol., 1985, 151:224-226.
Morgan, "A sling operation, using Marlex polypropylene mesh, for treatment of recurrent stress incontinence," Am. J. Obstet. GynecoL, 1970, 106(3):369-376.
Narik and Palmrich, "A simplified sling operation suitable for routine use," Am. J. Obstet. Gynecol., 1962, 84:400-405.
Nichols, "The Mersilene Mesh Gauze-Hammock for Severe Urinary Stress Incontinence," Obstet. Gynecol., 1973, 41(1):88-93.
Nicita, Giulio, (1998), "A New Operation for Genitourinary Prolapse," The Journal of Urology, 160:741-745.
Nickel et al., "Evaluation of a Transpelvic Sling Procedure With and Without Colpolsuspension for Treatment of Female Dogs With Refractory Urethral Sphincter Mechanism Incompetence," Veterinary Surgery, 1998, 27:94-104.
Norris et al., "Use of Synthetic Material in Sling Surgery: A Minimally Invasive Approach," J. Endocrinology, 1996, 10 (3):227-230.
Novak, "Abdonomovaginal Techniques," Gynecological Surgical Technique, 1977, Piccin Editore, Padua, 5 pages.
O'Donnell, "Combined Raz Urethral Suspension and McGuire Pubovaginal Sling for Treatment of Complicated Stress Urinary Incontinence," J. Arkansas Medical Society, 1992, 88(8):389.
Parra and Shaker, "Experience with a Simplified Technique for the Treatment of Female Stress Urinary Incontinence," British Journal of Urology, 1990, 66:615-617.
Pelosi II and Pelosi III, "New transobturator sling reduces risk of injury," Obg Management, 2003, pp. 17-37.
Pelosi III and Pelosi, "Pubic Bone Suburethral Stabilization Sling: Laparoscopic Assessment of a Transvaginal Operation for the Treatment of Stress Urinary Incontinence," Journal of Laparoendoscopic & Advanced Surgical Techniques, 1999, 9(1):45-50.
Penson and Raz, "Why Anti-incontinence Surgery Succeeds or Fails," Female Urology, 1996, Raz (ed.), W.B. Saunders Company, Chapter 41, pp. 435-442.

* cited by examiner

TISSUE SUPPORTED IMPLANTABLE DEVICE

IMPLANT

The present invention relates to an implant and a method for the treatment of vaginal and/or uterine prolapse and/or pelvic floor reconstruction. Prolapse is a relatively common condition, particularly amongst older women. It occurs when the pelvic floor muscles become weak or damaged and can no longer support the pelvic organs. These organs are then able to push against the walls of the vagina causing the women to feel discomfort and "something coming down".

Prolapse can be divided into a number of different categories according to the part of the vagina affected. Prolapse of the anterior (front) vaginal wall (cystourethrocoele) occurs when the bladder and/or the urethra push against and create a bulge in the front wall of the vagina. Prolapse of the posterior (back) vaginal wall can occur if the small intestine (enterocoele) or rectum (rectocoele) loses support and pushes against the back wall of the vagina. Uterine prolapse occurs when the womb drops down into the vagina and vault prolapse can occur in women who have had a hysterectomy.

Procedures have been developed to treat vaginal prolapse wherein, during surgery, mesh with long tails is used to attach the top of the vagina to the structurally defined tissues of the lower abdominal wall, the lumbar spine, or the ligaments of the pelvis. These tissues are comprised of dense, highly organised collagen. The mesh is typically introduced into the body through the vagina or an abdominal incision. Tethering of the vagina to these strong anchorage sites provides the vaginal wall with support. The disadvantage of this procedure is that the fixing of the mesh to these collagen dense tissues requires significant force to be employed by the surgeon to penetrate said tissue increasing the chance of tissue damage. Further, the sites of fixation can be highly innervated and vascularised, increasing the risk of trauma to the patient. Exit wounds through the abdomen or perineal skin may be required.

Typically, prior art devices used in the treatment of vaginal prolapse involve the anchoring of a support member in tissue types such as muscle, skin and cartilage, which have defined structures and comprise dense, highly organised collagen. The dense organised collagen makes these tissues, which are in fact resilient and hard to disrupt, difficult to penetrate. Thus to penetrate and anchor in such tissue requires an anchor to be sharp and/or requires a high force of insertion to be used. However, anchorage in structurally well defined tissue has conventionally been deemed advantageous, as anchors inserted in tissues with dense organised collagen provide a high retentive force against the implant being dislodged.

Recently, prolapse of the posterior vaginal wall has been treated by attaching a mesh to the posterior portion of the vagina while the other ends of the mesh extend through incisions in the perineum to anchor the mesh into layers of muscle, fascia and skin and thus secure the vaginal wall to defined structural tissues to provide the wall with support (Posterior intravaginal slingplasty (IVS) procedure). This procedure suffers from the disadvantage that the exit incisions or wounds in the perineum are close to the anus. These incisions may act as a portal for infection by colonic bacteria.

The present invention overcomes some of the problems associated with implants currently used to treat vaginal prolapse and pelvic floor repair.

The inventor of the present application has surprisingly found that it is not essential to penetrate structurally defined tissues In order to anchor an implant such that it can provide suitable support to the vaginal wall. Instead, the inventor has developed an implant which may be successfully anchored in the structurally undefined fibro-fatty tissue of the pelvic paravaginal tissues for example the fibro-fatty tissue within the retropubic, paraurethral, or pararectal space and ischiorectal fossa and which is adequate to ensure that the implant is capable of supporting the utero/vaginal tissues.

Thus, according to a first aspect of the invention there is provided an implant for use in vaginal wall support comprising (i) a vaginal support member substantially sized and/or shaped to the portion of the vaginal wall to be supported and (ii) at least two extension portions projecting from the support member; wherein at least one extension portion has fixation means for anchoring the extension portion into pelvic paravaginal fibro-fatty tissue without being fixed into defined structural tissues.

Preferably, in use, the implant may be anchored solely in the paravaginal fibro-fatty tissue without any need for extension portions or fixation means to fix into such defined structural tissues.

Pelvic paravaginal fibro-fatty tissue is fibro-fatty tissue which lies against or to the side of the vagina. Such tissue includes the fibro-fatty tissue of the retropubic space, paraurethral space, pararectal space and/or ischio-rectal fossa.

The retropubic space is defined by an antero-superior boundary which is the peritoneum and rectus sheath and an interior boundary of endopelvic fascia. The space defined by these boundaries is medially filled by the bladder, the urethra, fibro-fatty tissue and blood vessels. The blood vessels of the retropubic space generally become larger both in a superior and lateral direction within the retropubic space. The retropubic space extends approximately 8 cm from the endopelvic fascia to the rectus sheath, this distance varying by around 2 cm depending on the individual.

The paraurethral space is comprised of fibro-fatty tissue which lies against or to the side of the urethra.

The pararectal space is comprised of fibro-fatty tissue which lies against or to the side of the rectum.

The ischio-rectal fossa is a wedge shaped space filling in the lateral part of the anal triangle and extending forwards into the uro-genital triangle. Its lateral wall is formed by the fascia over the lower part of obturator internus, the falciform margin of the sacro-tuberous ligament and the tuber ischii. Medially the two fossae are separated by the perineal body, the anal canal and the anococcygeal body, and they are roofed in by the downward sloping levator ani muscles of the pelvic floor.

In the context of the present invention, defined structural tissues comprise tissues which comprise substantially organised collagen. For example, such tissues include the rectus fascia, pubic bone, Coopers ligament, sacrospinous ligament, skin, muscle and other fascia as well as other cartilage, bone, muscle or fascial tissues.

In contrast to defined tissues such as cartilage, bone or muscle, the pelvic paravaginal fibro-fatty tissues lack substantial organised collagen. This fibro-fatty tissue has a sponge or foam like consistency.

Fixation of the fixation means in pelvic paravaginal fibro-fatty tissue is advantageous as it allows positioning of the support member at a portion of the vaginal wall to be repaired even if the central vaginal tissue is not suitable for attachment of the support. Such circumstance may arise for example in paravaginal prolapse where a lateral defect is present or in more severe cases of prolapse.

The use of an implant which is supported by such tissue provides a number of advantages over the prior art. For example, implants of the invention are advantageous as fixation does not require exit incisions or wounds as required for posterior intravaginal slingplasty (IVS). Moreover, anchorage of an implant in the pelvic paravaginal fibro-fatty tissue avoids complications associated with bone anchorage and the pain associated with anchorage into structurally defined tissues.

As the fibro-fatty tissue is not as hard or as resilient as tissues such as muscle, skin or cartilage, insertion of an extension portion and fixation means of the implant of the invention in the fibro-fatty tissue only requires a low force. However, in order to provide anchorage in pelvic paravaginal fibro-fatty tissue it is important that, during insertion of fixation means the tissue is minimally disrupted.

Accordingly, in one embodiment, in use, the fixation means are provided in a first arrangement to allow insertion and retraction of the fixation means within the paravaginal fibro-fatty tissue whilst causing minimal tissue disruption and when suitably located the fixation means adopt a second arrangement wherein the fixation means grip the pelvic paravaginal fibro-fatty tissue.

The movement between the first arrangement and the second arrangement is preferably an active movement which is controlled by the surgeon during insertion, positioning and placement of the implant, rather than movement merely arising from the action of the surrounding tissue during insertion, positioning and placement of the fixation means of the implant.

Any suitable fixation means which are suitable for anchoring the extension portions in the fibro-fatty paravaginal tissue may be used.

In particular embodiments of the implant the fixation means may comprise adhesive portions and/or means shaped to grip the fibro-fatty tissue.

Any suitable adhesive may be used. For example, the adhesive may be one or more of cyanoacrylate, fibrin, albumin or gelatin based glues.

The adhesive may be provided such that in a first arrangement, it cannot interact with the pelvic paravaginal fibro-fatty tissue during placement of the implant and in a second arrangement, when the implant is suitably located, the adhesive is available for fixing to the surrounding pelvic paravaginal fibro-fatty tissue.

For example, the adhesive may be encapsulated within a capsule (a first arrangement of the fixation means) such that the adhesive cannot interact with the tissue during placement of the implant. When the implant is suitably located, the capsule of adhesive may be made to release the adhesive and allow the implant to be fixed to the surrounding tissue (a second arrangement).

Alternatively the adhesive may be activated by any suitable means, for example heat, light, cold or ultrasound. The implant can be moved into the pelvic paravaginal fibro-fatty tissue, for example the tissue of the pararectal space with the adhesive being provided in a first arrangement in which it is unable to adhere the implant to the surrounding tissue then, following the activation of the adhesive or change in state of the adhesive by some means, for example but not limited to heat, light, cold or ultrasound, the adhesive will adopt a second arrangement wherein it can adhere the fixation means of the implant to the surrounding tissue.

In particular embodiments of the implant the fixation means are resiliently deformable such that, in use, the fixation means are in a resiliently deformed position (a first arrangement) when inserted into the pelvic paravaginal fibro-fatty tissue and when being suitably positioned in the tissue. Positioning may involve bi-directional movement of the fixation means (repeated insertion and retraction of the extension portions and fixation means into the tissue). In the first arrangement, during insertion and placement, the fixation means do not grip the surrounding tissue and cause minimal tissue disruption.

When suitably located, the deformed fixation means can be released such that they adopt a second arrangement wherein the fixation means grip the tissue.

In embodiments wherein the fixation means comprise adhesive, the fixation means may be deformed such that on insertion and positioning of the fixation means, the adhesive is not in contact with the surrounding tissues. In such embodiments, only on release of the fixation means, such that they adopt a second arrangement, will the adhesive come into contact with the surrounding tissue and enable the fixation means to grip the surrounding pelvic paravaginal fibro-fatty tissue.

This has the advantage that insertion and positioning of the fixation means in a deformed arrangement causes minimal tissue disruption.

Preferably the fixation means comprise shaped means to anchor in the pelvic paravaginal fibro-fatty tissue.

Preferably at least part of the fixation means is shaped such that it can recoil from a deformed shape, which allows insertion and positioning of the fixation means in the pelvic paravaginal fibro-fatty tissue whilst causing minimal tissue disruption, to a resting shape in which the fixation means extend into the fibro-fatty tissue and grip the fibro-fatty tissue to inhibit retraction of the fixation means.

In one embodiment the fixation means comprise a substantially triangular portion of polymer tape wherein resistance against retraction of the fixation means from the fibro-fatty tissue is provided by the base of the triangular shaped polymer tape. In use, such an embodiment of the fixation means may be inserted into the pelvic paravaginal fibro-fatty tissue in a deformed arrangement, for example wherein the points at the base of the triangular shaped polymer tape are folded or rolled towards the centreline which extends perpendicularly from the base. Once inserted and suitably positioned, the fixation means are released such that the points at the base of the triangular shaped polymer tape extend away from the centreline and move into the surrounding tissue.

In this embodiment of the fixation means, resistance of the fixation means in the surrounding tissue is provided only at a single level.

Alternatively, the fixation means may be shaped such that when released from their deformed arrangement the fixation means adopt a substantially Y, 7, T, arrowhead, or a 3, 4 or more membered cloverleaf shape. In use, during insertion and positioning, these embodiments of fixation means are deformed such that they resemble a single member with substantially no projections extending therefrom. On release of the fixation means from the deformed shape the second arrangement adopted by the fixation means causes the fixation means to have increased resistance to retraction of the fixation means from the pelvic paravaginal fibro-fatty tissue tissue. Depending on the shape adopted by the fixation means following release from their deformed shape, fixation may be achieved a plurality of levels in the surrounding tissue.

The fixation means may be provided as a loop of suitable mesh material wherein during insertion of the loop into the fibro-fatty tissue the mesh is dragged into the tissue and on release of the loop the mesh is held in the fibro-fatty tissue with the plurality of strands of the mesh providing sufficient surface area such that retraction of the fixation means from the tissue is resisted by the tissue.

In embodiments of fixation means utilizing mesh material, the mesh, once suitably positioned, may be moved from a first arrangement which causes minimal tissue disruption during insertion to a second arrangement which provides improved resistance compared to the first arrangement.

In such embodiments a deformable plastics material, metal or memory metal may be surrounded by a mesh material such that when the fixation means is suitable positioned, the plastics material, metal or memory metal is released such that the mesh is moved to a second arrangement wherein the mesh adopts a shape of increased resistance to retraction of the fixation means from the surrounding tissue.

In particular embodiments the terminal ends of mesh extension portions may be expanded to provide a bulbous or T shaped terminus.

In one embodiment of the implant, the fixation means comprise a generally planar sheet comprising a series of truncated triangular sections extending proximally from a substantially blunt tip.

More preferably the triangular sections increase in surface area from the tip of the fixation means furthest from the support towards the support such that the fixation means are inwardly tapered in the direction of insertion to facilitate insertion and maximise the force required for retraction of the fixation means following insertion i.e. the point of the triangle is inserted in the tissue before the base.

As discussed above in relation to the triangular shaped polymer tape embodiment of fixation means, the triangular sections may be rolled or folded such that insertion of the triangular sections and their bidirectional movement in the tissue during suitable positioning of the fixation means causes minimal tissue disruption, whilst on release of the fixation means from the deformed shape the multiple triangular sections provide multiple sites of fixation at a plurality of layers of tissue such that additive fixation in the pelvic paravaginal fibro-fatty tissue is achieved. Although each fixation point may be weak, overall, it is possible to provide sufficient anchorage to provide sufficient support to the vaginal wall.

Preferably the fixation means provide multiple levels of fixation within the pelvic paravaginal fibro-fatty tissue tissue. In embodiments of fixation means comprising adhesive, preferably the adhesive provides multiple sites of fixation at a plurality of tissue layers.

The fixation means may be held in a deformed arrangement during insertion and positioning in the pelvic paravaginal fibro-fatty tissue by an insertion tool.

In the deformed arrangement the position of the fixation means in the fibro-fatty tissue and/or the tension provided to the vaginal support member may be adjusted whilst only causing minimal tissue disruption.

A plurality of fixation means may be provided on each extension portion.

Thus in one embodiment, the total number of fixation sites in each implant is 4 or more, eg 6 or more, 8 or more, 10 or more, or 12 or more.

Preferably each fixation means is less than or equal to 2 cm in length and 1 cm in width.

In particular embodiments of the implant the extension portions are provided by polymer mesh. Optionally the extension portions may be provided by sutures or by a flat or filiform means.

Preferably the extension portions are flexible.

This is advantageous as an extension portion will be able to bend without breaking as it is inserted into the paravaginal fibro-fatty tissue and the extension portion will minimally disrupt the fibro-fatty pelvic paravaginal tissue during insertion. In addition, there will be only a minimal chance of damage being caused to tissues in the paravaginal or pelvic region.

Preferably the implant comprises a plurality of extension portions. For example, the implant can comprise 3, 4, 5, 6, 7, 8, 9, 10 or more extension portions. Each extension portion may comprise a single fixation means or a plurality of fixation means, A plurality of extension portions are advantageous as they can each be used to provide an additive amount of support to the vaginal support member. As the total amount of support required to be provided by a vaginal support member will be relatively constant, in embodiments of the implant comprising a plurality of extension portions, each of the extension portions and fixation means are required to provide less support. Thus, either one of or both of the extension portions and fixation means may be smaller and comprise less mass.

This may be advantageous in reducing the foreign body response of the body against the implant.

Preferably multiple pairs of extension portions may be provided.

In a first embodiment at least 2 extension portions are provided on the implant. In an alternative embodiment at least 4 extension portions are provided. In a further alternative embodiment at least 6 extension portions are provided. In a further alternative embodiment at least 8 extension portions are provided.

Multiple pairs of extension portions which project from the support member are advantageous as they allow the vaginal support member to be placed over the tissue to be repaired and the extension portions to be more easily inserted around the repair site in a balanced manner to suitably locate the support member on the vaginal wall.

In particular embodiments of the implant comprising a plurality of extension portions, each of the multiple extension portions may be joined at any point or region along their length to another extension portion. The point or region where the extension portions are joined may be used to move the extension portions into the tissue during insertion.

For example two extension portions may project from two distinct points or regions of the support member, the two extension portions each joining one another at a point or region distinct from the support. This is advantageous as it allows insertion of more than one extension portion using only one insertion point and thus minimises disruption to the tissue during insertion.

In particular embodiments of the implant the extension portions include loops of material which, in use, are used to push the extension portions into the tissue. Alternatively the extension portions comprise slots in which an insertion tool can be inserted.

In such embodiments, in use, the slots or loops aid positioning of the extension portions in the pelvic paravaginal tissue, via an insertion tool.

Preferably the extension portions are less than or equal to 500 µm in thickness. This has the advantage that minimal tissue disruption occurs on insertion of the extension portions.

Further, using extension portions of less than or equal to 500 µm in thickness minimal foreign body mass is introduced into the body of the patient, reducing the likelihood of infection and erosion of surrounding tissues.

Preferably the distance from the support member to the tip of the extension portion, not including the width of the support, is in the range of 1 cm to 10 cm. More preferably the distance from the support member to the tip of the extension portion, not including the width of the support, is in the range of 1 cm to 8 cm, more preferably 4 cm to 8 cm.

These ranges of lengths are advantageous as they ensure that an extension portion cannot be inserted too far into the body and penetrate structurally defined tissues such as the rectus sheath or highly innervated and/or vascularised tissues close to the abdominal wall or perineum. Thus, pain and visceral damage to the patient are minimised.

In a particular embodiments of the implant, an extension portion has a width of less than or equal to 15 mm, more preferably the width of an extension portion is in the range 8 to 10 mm.

In embodiments of the implant wherein, for example, an extension portion is provided by a suture the width of an extension portion is equal to or less than 0.5 mm.

Different widths of extension portions may be used in one implant in combination as required.

In particular embodiments of the implant the utero/vaginal support member is elliptical in shape. This may be advantageous in the support of anterior prolapse, as the support will therefore more closely resemble the shape of the tissue of the anterior vaginal wall. Alternatively, the vaginal support may be an ellipse or a truncated ellipse. In alternative embodiments, the support member is ovoid in shape. This may be advantageous in the treatment of posterior prolapse as the support will more closely resemble the shape of the tissue of the rectocoele.

In a further alternative embodiment the support member may be bifurcated, H or frog shaped such that it comprises at least two zones which, when the implant is in use, can be positioned on the vaginal wall such that the zones are arranged to pass around the urethra. This shape may be advantageous to provide support to tissue on either side of the urethra.

It will be understood that the support member may be, for example square, rectangular, elliptical, or of any other suitable shape as required to repair the weakened tissue.

In preferred embodiments of the implant the vaginal support member has a width in the range 3 cm to 8 cm.

In preferred embodiments of the implant the vaginal support member has a length in the range 4 cm to 12 cm.

The vaginal support member requires to be a sufficient size that support is substantially provided across the area of the prolapse.

A wide variety of materials may be used to form the implant. Suitable materials include, but are not limited to, tissue grafts, suitable synthetic material, including plastics, polypropylene, MINIMESH™ (Mpathy Medical Devices Limited, Glasgow), or polyester. The material may be absorbable, resorbable or non-absorbable. Optionally some portions of the implant may be absorbable or resorbable and other portions non-absorbable. The implant may be integral or a composite of different parts. The whole implant may be formed from the same material or alternatively different parts of the implant may be formed from different materials.

In particular embodiments the implant is formed from materials, or use technologies, which provide temporary substance to the implant to improve its surgical handling characteristics, for example, reducing any rough edges on the implant and improving its tackiness to assist in positioning of the support on the vaginal wall. This includes absorbable coatings or a layer applied to at least one face of the implant which may add bulk to the implant and make it easier to handle. Suitable absorbable coatings or layers can be manufactured from or comprise plastics, hydrogels, gelatin, starch or cellulose based hydrogels, alginate, polylactic acid, polyglycolic acid or hyaluronic acid. As an alternative, or in addition to the coating or layer, the implant may be formed from biocomponent microfibres which include a core material and surface material, for example a polypropylene core and polylactic or polyglycolic acid surface. In particular the implant may be formed with DUAL PHASE TECHNOLOGY™ provided by Mpathy Medical Devices Limited (Glasgow, UK).

In particular embodiments the fixation means and/or the extension portions and/or the support member of the implant are formed from absorbable material. Resorbtion or absorption of the implant or at least part of the implant, for example the support member, into the surrounding tissues preferably takes at least 3 months, more preferably at least 6 months, most preferably at least 12 months.

Resorption or absorption of the implant over time is advantageous, as the amount of foreign material in the body is reduced, thus minimising the likelihood of the patient developing complications associated with the presence of foreign material in the body.

It is advantageous if the material from which the support and/or the extension portions is formed has a low mass density to minimise the amount of foreign material in the body such that the risk of infection and discomfort to the patient is reduced.

In preferred embodiments the support member and/or the extension portions comprises a mesh material.

Preferably the support member comprises mesh material having a mass density of less than 50 $g/m^2$, more preferably less than 30 $g/m^2$, more preferably less than 25 $g/m^2$ and most t preferably less than 20 $g/m^2$.

In a particularly preferred embodiment the support member comprises strands and includes major spaces and pores. In one embodiment the strands of the mesh may be formed by at least two filaments, the major spaces formed between the strands which provide the surgical implant with the necessary strength, the filaments arranged such that pores are formed in the strands of the mesh. In an alternative embodiment the strands may be formed by monofilaments which form loops which give rise to the pores.

Preferably the strands are spaced apart to form major spaces of between 1 mm to 10 mm. This is advantageous as such spaces help to reduce the mass of the mesh whilst providing the mesh with sufficient tensile strength to secure the tissue defect being repaired by the mesh. More preferably the strands are spaced apart to form major spaces of between 2 mm to 8 mm. Preferably the strands have a diameter of less than 600 μm.

The strands and filaments are preferably warp knit. In a particular embodiment the strands are arranged to form a diamond net mesh. In an alternative embodiment the strands are arranged to form a hexagonal net mesh. Preferably the strands are arranged to form a net mesh which has isotropic or near isotropic tensile strength and elasticity.

Preferably the filaments have a diameter of between 0.02 mm to 0.15 mm. More preferably the filaments of the mesh are of a diameter 0.06 mm to 0.1 mm.

As tissue may be slow to grow into an implant comprised of mesh which includes narrow members spaced apart by relatively wide gaps or major spaces, it is desirable to provide pores in the strands of the mesh to which tissue may more easily adhere and aid tissue in growth. These pores may be provided by at least two filaments being interwoven/knitted to produce strands of the mesh comprising pores. Alternatively, one filament can be knotted or twisted to form pores of suitable dimensions.

Preferably the pores in the strands are between 50 to 200 μm in diameter. More preferably the pores are of between 50 to 75 μm in diameter. These pore sizes enable efficient fibroblast through growth and ordered collagen laydown in order to provide optimal integration into the body.

Preferably the perimeter of a mesh implant is bound by a member such that, for example, when in use the support member is positioned on the vaginal wall, the strands of the mesh do not protrude into the surrounding tissue which may be delicate and sensitive. This is advantageous as any such protrusions may cause discomfort to the patient.

In particular embodiments, the implant is comprised of mesh material as described in International Application WO 02/078568 (e.g. MINIMESH™ (Mpathy Medical Devices Limited, Glasgow)).

The extension portions may be formed from different material to the support member. Alternatively, the extension portion may be comprised of the same material as the support member.

In preferred embodiments the extension portions of the implant are absorbable. Preferably the extension portions are comprised of a carbohydrate or starch material which can be absorbed into the body over a defined time period.

In particular embodiments the support member and/or the extension portions of the implant comprises medicament. For example the support and/or the extension portions may be provided with an antimicrobial medicament. In a particular example the support or extension portions are coated with a medicament, for example an antimicrobial.

According to a second aspect of the invention there is
  provided a method of supporting all or part of a vaginal wall comprising the steps of
  positioning a surgical implant comprising a first aspect of the invention on the vaginal wall,
  inserting the first extension portion into a paravaginal fibro-fatty tissue without extending through or being fixed into defined structural tissue or having skin exit wounds,
  inserting the second extension portion into a paravaginal fibro-fatty tissue without extending through or being fixed into defined structural tissue or having skin exit wounds, such that the vaginal support member is suspended from the first and second extension portions and supports the vaginal wall.

In particular embodiments of the method at least one or both of said first or second extension portion(s) is inserted into the tissues of the retropubic space, paraurethral space, pararectal space and/or ischio-rectal fossa.

The method may include further steps of adjustment of the placement of the fixation means in the tissue. Such movement may be bi-directional in an insertion direction and a retraction direction.

In particular embodiments of the implant comprising more than two extension portions, the method comprises additional steps to insert each of the extension portions into the pelvic paravaginal fibro-fatty tissue without extending through or being fixed into defined structural tissue or having skin exit wounds.

For anterior vaginal wall prolapse or cystourethracoele, where the bladder and urethra are the prolapsing organs, the extension portions are positioned into the tissues of the retropubic space.

For posterior prolapse, especially rectocoele, where the prolapsing organ is the rectum, the extension portions extend into the pararectal space and ischio-rectal fossa. For high posterior prolapse (enterocoele) or vault prolapse the extension portions extend into the pararectal space. In addition, a more cephalad course towards, but not ending in, the sacrospinous ligaments may be employed.

Preferably at least one extension portion is located above the endopelvic fascia if the implant is positioned in an anterior position.

Preferably when the implant is positioned at a posterior position at least one extension portion is located in the pararectal space.

It is advantageous in the treatment of anterior prolapse to locate the extension portions above the endopelvic fascia and/or into the abdominal pressure compartment as then during periods of raised abdominal pressure, for example coughing or sneezing, the increase in pressure is transmitted to the implant such that the implant is more able to provide support to the utero/vaginal tissues.

Preferably the extension portion is inserted into the pelvic paravaginal soft tissue using an insertion tool.

According to a third aspect of the invention there is provided the use of an implant of the present invention for treatment of utero/vaginal prolapse and/or pelvic floor reconstruction.

According to a fourth aspect of the invention there is provided a kit comprising an implant for use in vaginal wall support comprising a vaginal support member substantially sized and/or shaped to the portion of the vaginal wall to be supported and at least two extension portions projecting from the support member, wherein at least one extension portion has fixation means for anchoring the extension portion into pelvic paravaginal fibro-fatty tissue without being fixed into defined structural tissues and an insertion tool.

Typically the insertion tool is a needle shaped surgical steel tool to which the extension portions can be releasably mounted. The insertion tool may be curved and have handle means to aid positioning of the extension portions in the body.

The insertion tool can be of various lengths and curvatures as required for insertion of the anchors of the implant into the tissue.

Preferably the tool comprises jaw means between which the fixation means of the implant can be releasably held, the jaw means being moveable by the surgeon when the fixation means are in position. Alternatively, the tool may comprise a collar which shields the surrounding tissue from the fixation means during insertion of the fixation means into the pelvic paravaginal tissue.

In a further alternative embodiment the tool may comprise a collar which constrains the deformed arrangement of the fixation means during insertion of the fixation means into the pelvic paravaginal tissue.

The tool typically comprises an elongate shaft of length 6 to 15 cm which may include a semi-blunt or sharp point at a first end and a handle at a second end and holding means to releasably attach the shaft to the implant. The tool can be used to releasably hold the fixation means of the implant in a deformed arrangement during insertion and placement of the fixation means. To releasably hold the fixation means, the tool may be provided with a releasable collar or jaw means which can be actuated by the surgeon to release the fixation means from their deformed arrangement.

The elongate shaft of the tool may be curved or bent, through an angle of approximately 30°. In particular embodiments of the tool, the tool has a length of 8 cm. In embodiments of the tool, the elongate shaft of the tool is between 2 to 4 mm in diameter.

The tool may be formed from any suitable material such as plastics material or surgical steel and may be for single patient use or for repeated use with multiple patients Embodiments of the present invention will now be described by way of example only, with reference to the accompanying drawings in which FIG. 1 is a plan view of a first embodiment of an implant of the present invention;

Figure 1:
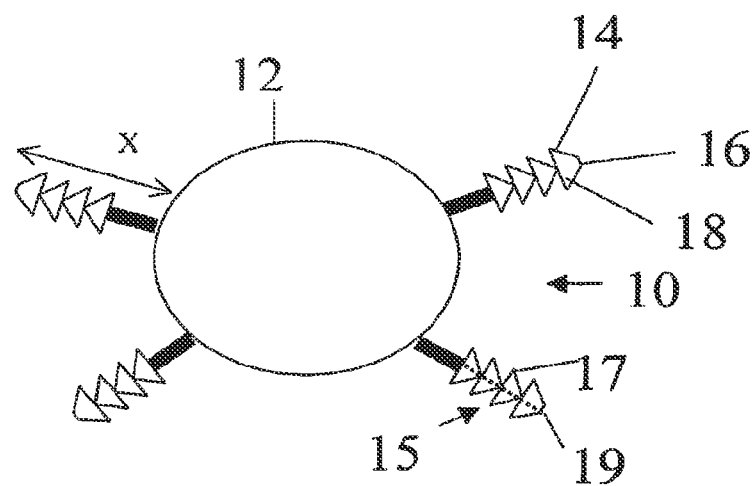

As shown in FIG. 1 (not to scale), in one embodiment the implant 10 comprises a thin flexible vaginal support member 12, which is sized and/or shaped to the portion of the vaginal wall to be supported, for example, as shown, the support member may be substantially circular shaped and be of width in the range 3 to 8 cm and length in the range 4 to 12 cm.

Figure 3:
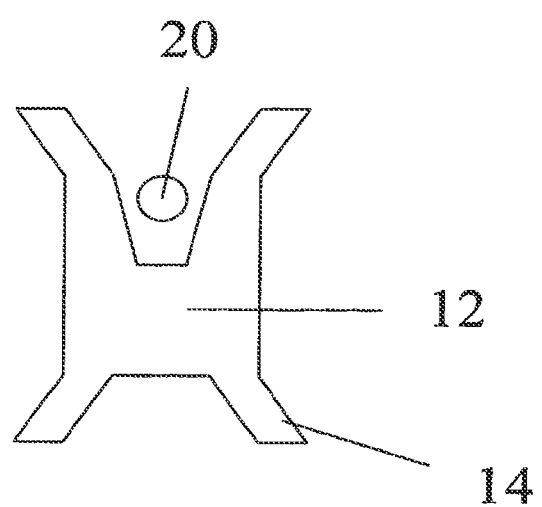
FIG. 3 is a plan view of a third embodiment of a bifurcated implant of the present invention.
Figure 4:
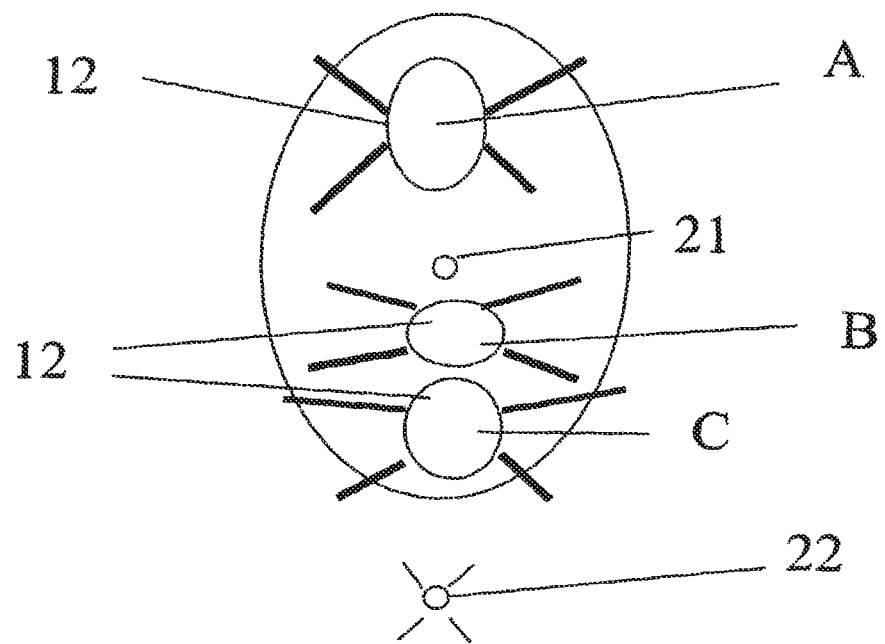
FIG. 4 is an illustration of an implant of the present invention in use to treat an anterior (front) vaginal wall prolapse (cystouethrocoele) (A), an implant of the present invention in use to treat rectocoele (B) and an implant of the present invention in use to treat a enterocoele (C)
Figure 5:
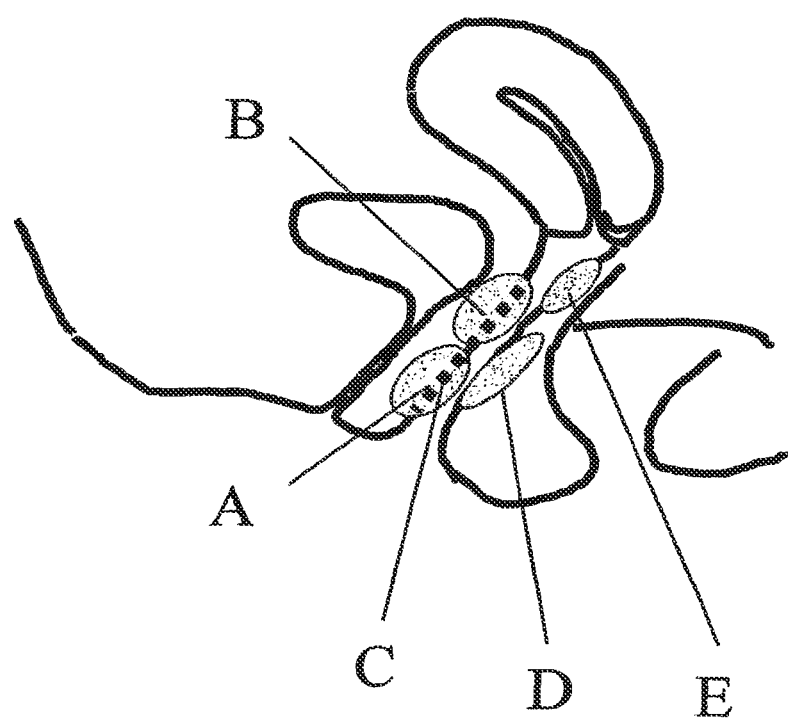
FIG. 5 is an illustration of the position of A—urethrocoele, B—cystocoele, C—cystourethrocoele, D—rectocoele and E—enterocoele.

Although in the embodiment shown in FIG. 1 the vaginal support member is substantially circular, the support can be of any suitable shape for application to the tissue to be repaired. For example, in another embodiment the support may be substantially rectangular as in FIG. 2. In another embodiment the implant is H or frog shaped as in FIG. 3 to allow the implant to extend around the urethra 20. The implant may be elliptical or ovoid shape as shown in FIG. 4. Different shapes of support member are advantageous depending on the position of vaginal tissue being supported, for example depending on whether the vaginal tissue is in front of the cervix 21 or posterior prolapse to support the back vaginal wall.

Extension portions 14 project from the vaginal support member 12.

The extension portions may be provided by any suitable means, for example by polymer tape, in particular polypropylene tape or by sutures. An extension portion (shown by X in FIG. 1) is less than 12 cm in length such that the extension portions and fixation means do not extend into defined anatomical structures or exit the body. However, the extension portions may be shorter depending on the depth of fixation desired, for example less than 8 cm, less than 6 cm, less than 4 cm or less than 2 cm.

Figure 2:
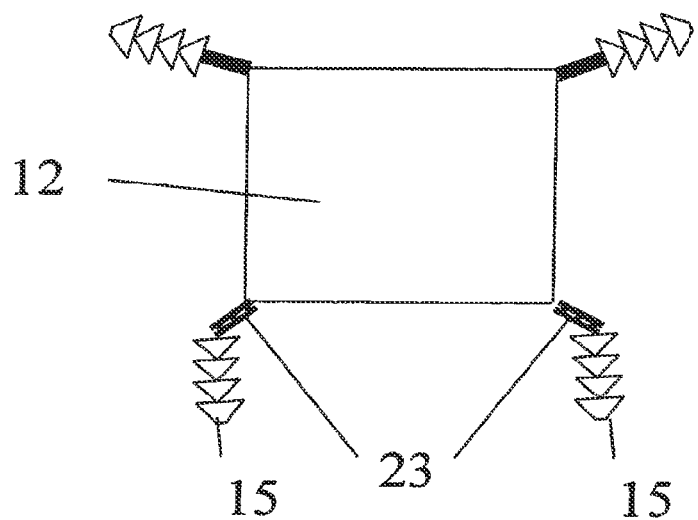
FIG. 2 is a plan view of a second embodiment of an implant of the present invention.

The extension portions comprise fixation means 15 which allow fixation of the fixation means to the pelvic paravaginal fibro-fatty tissue without requiring penetration of structurally defined anatomical structures, The fixation means may extend along the longitudinal axis of the extension portions as illustrated in FIG. 1 or the fixation means may be angled from the longitudinal axis 23 of the extension portions as illustrated in FIG. 2.

In the embodiments of the implant illustrated in FIGS. 1 and 2, the fixation means are provided by polymer tape shaped as a series of truncated triangular sections extending proximally from a substantially blunt tip 16. The triangular sections of the polymer tape may be of equal size as illustrated or increase in surface area from the blunt tip 16 of the extension portion furthest from the support member towards the support member such that the extension portions are inwardly tapered in the direction of insertion to facilitate insertion and minimise retraction of the extension portions following insertion i.e. the blunt tip 16 of the triangle is inserted in the tissue before the base of the triangle 18.

It is important that minimal disruption of the pelvic paravaginal fibro-fatty tissue for example of the retropubic, paraurethral, or pararectal space or ischio-rectal fossa around the fixation means and extension means occurs during insertion of the fixation means. To aid insertion and positioning, which typically requires bi-directional movement of the fixation means in insertion and retraction directions, the fixation means in the embodiments shown are resiliently deformable such that they adopt, and can be held in a deformed arrangement during insertion and positioning of the fixation means. In the embodiment shown, the points 17 along the edges of the triangular sections of the fixation means are folded or rolled towards the centreline of the fixation means, indicated by the dashed line 19, such the deformed arrangement of the fixation means when inserted into the tissue promotes minimal tissue disruption. When suitably located in the tissue, the fixation means are actively released to adopt a second arrangement in which, due to the resilient nature of the deformation, they uncurl or unfold into the surrounding tissue and grip the tissue. As the fibro-fatty tissue is of sponge or foam like consistency there is no requirement for the fixation means to be sharp to penetrate the surrounding tissue or for high force to be used to allow the fixation means to penetrate the tissue.

The released fixation means inhibit the retraction of the fixation means from the tissue due to the resistance provided by the fixation means in the fibro-fatty tissue.

In use, the implant of the present invention is inserted by
exposing, through a vaginal incision alone, without abdominal or perineal exit wounds or organ damage, the segment of vaginal wall and secondary organ prolapse,
placing the appropriately shaped and/or sized vaginal support member on the vaginal wall,
inserting said first extension portion into pelvic paravaginal fibro-fatty tissue without being fixed into defined structural tissue,
inserting said second extension portion into pelvic parvaginal fibro-fatty tissue without being fixed into defined structural tissue,
inserting any further extension portions into pelvic paravaginal tissue without being fixed into defined structural tissue, adjustment of fixation means of the above extension portions by means of bi-directional movement of the fixation means in the tissue to obtain suitable placement and tension, and
closure of the vaginal skin and appropriate suture repair of the defect.

The method may optionally include the step of suture fixation of the support member, for example to the vaginal wall.

To treat anterior vaginal prolapse the extension portions can be placed in the retropubic soft tissue along the paraurethral tunnel or more laterally, along a similar initial route as taken during a trans-obturator approach, towards the obturator foramen. However, whichever route the extension portions take they are not located into structurally defined tissues comprising dense organised collagen, they do not exit the body or fix to bone.

In use, to treat posterior vaginal prolapse the support is positioned on the vaginal tissue to be repaired and then the support is secured by inserting the extension portions into the soft tissue of the pararectal or ischiorectal fossa. Unlike conventional posterior IntraVaginal Slingplasty (posterior IVS) the extension portions do not require to be fixed in defined anatomical structures and thus do not require incisions near the anus 22 or in the perineum to be made. Thus, the chance of infection i.e. anaerobic infection from the colon and other associated problems relating to these incisions when used for posterior IVS do not apply to the present invention, Thus, in contrast to anchors described in the art for anchoring an implant in defined anatomical structures such as fascia, bone or skin which bite into the structurally defined tissue to resist retraction, the extension portions of the present invention do not cut into the tissue, but provide a resistive force in the tissue. As previously described, this resistive force is typically provided a multiplicity of levels in the tissue to provide additive traction.

Insertion and positioning of the implant may be performed using an insertion tool. When a tool is used, the method may include a step of releasing the fixation means from the tool.

Although the invention has been described in terms of particular embodiments and applications, one of ordinary skill in the art will appreciate that various modifications can be made without departing from the scope of the invention.

The invention claimed is:

1. A tissue supported implantable device comprising:
   a support member; and
   an extension portion projecting from the support member and having a barbed fixation section that is adapted to anchor the extension portion into pelvic paravaginal tissue, the barbed fixation section provided to allow bi-directional adjustment of the barbed fixation section relative to the pelvic paravaginal tissue, and when suitably located, the barbed fixation section engages the pelvic paravaginal tissue.

2. The implantable device of claim 1, wherein the pelvic paravaginal tissue is fibro-fatty tissue.

3. The implantable device of claim 1, wherein the pelvic paravaginal tissue is tissue of the retropubic space.

4. The implantable device of claim 1, wherein the pelvic paravaginal tissue is tissue of the paraurethral space.

5. The implantable device of claim 1, wherein the pelvic paravaginal tissue is tissue of the pararectal space.

6. The implantable device of claim 1, wherein the pelvic paravaginal tissue is tissue of the ischiorectal fossa.

7. The implantable device of claim 1, wherein the pelvic paravaginal tissue is fibro-fatty tissue alongside of the vagina.

8. The implantable device of claim 1, wherein the barbed fixation section is adapted for anchoring the extension portion into pelvic paravaginal tissue without a skin exit wound.

9. The implantable device of claim 1, comprising multiple extension portions, each extension portion projecting from the support member and each extension portion having a barbed fixation section.

10. The implantable device of claim 1, wherein the support member comprises a mesh material having a mass density of less than 50 g/m².

11. The implantable device of claim 1, wherein the support member comprises a mesh material having a mass density of less than 30 g/m².

12. The implantable device of claim 1, wherein the support member comprises a mesh material having a mass density of less than 25 g/m².

13. The implantable device of claim 1, wherein the support member comprises a mesh material having a mass density of less than 20 g/m².

14. A tissue supported implantable device comprising:
    a support member; and
    a first extension portion projecting from a first side of the support member and a second extension portion projecting from a second side of the support member, each of the first extension portion and the second extension portion including a barbed fixation section that is configured to secure a respective one of said extension portions into pelvic paravaginal tissue;
    wherein the barbed fixation section is configured to allow bi-directional adjustment of the barbed fixation section relative to the pelvic paravaginal tissue, and when suitably located, the barbed fixation section engages the pelvic paravaginal tissue.

15. A tissue supported implantable device comprising:
    a support member comprising a mesh material having a mass density in a range between 20 g/m² and 50 g/m²; and
    a first extension portion projecting from a first side of the support member and a second extension portion projecting from a second side of the support member, each of the first extension portion and the second extension portion including a barbed fixation section that is configured to secure a respective one of said extension portions into pelvic paravaginal tissue;
    wherein the barbed fixation section is configured to allow bi-directional adjustment of the barbed fixation section relative to the pelvic paravaginal tissue, and when suitably located, the barbed fixation section engages the pelvic paravaginal tissue.

* * * * *